US010966819B2

(12) United States Patent
Goldshleger et al.

(10) Patent No.: US 10,966,819 B2
(45) Date of Patent: Apr. 6, 2021

(54) COMPOSITE LIGHT ADJUSTABLE INTRAOCULAR LENS

(71) Applicant: RxSight, Inc., Aliso Viejo, CA (US)

(72) Inventors: Ilya Goldshleger, Ladera Ranch, CA (US); John Kondis, Irvine, CA (US); Ronald M. Kurtz, Irvine, CA (US); Ritu Shrestha, Huntington Beach, CA (US); Gergely T. Zimanyi, Berkeley, CA (US)

(73) Assignee: RxSight, Inc., Aliso Viejo, CA (US)

( * ) Notice: Subject to any disclaimer, the term of this patent is extended or adjusted under 35 U.S.C. 154(b) by 0 days.

(21) Appl. No.: 15/607,681

(22) Filed: May 29, 2017

(65) Prior Publication Data

US 2018/0338827 A1 Nov. 29, 2018

(51) Int. Cl.
*A61F 2/16* (2006.01)
*G02C 7/02* (2006.01)

(52) U.S. Cl.
CPC .......... *A61F 2/1659* (2013.01); *A61F 2/1648* (2013.01); *A61F 2/1627* (2013.01); *A61F 2002/169* (2015.04); *A61F 2002/1682* (2015.04); *A61F 2002/1686* (2013.01); *A61F 2002/1696* (2015.04);
(Continued)

(58) Field of Classification Search
CPC .................. A61F 2/1659; A61F 2/1648; A61F 2002/169; A61F 2002/1696; A61F 2210/0076; A61F 2/1627; A61F 2/1602; A61F 2/161; A61F 2002/1682;
(Continued)

(56) References Cited

U.S. PATENT DOCUMENTS 5,288,293 A * 2/1994 O'Donnell, Jr. ...... A61F 2/1613
623/6.22
5,712,721 A * 1/1998 Large .................... A61F 2/1613
351/158
(Continued)

FOREIGN PATENT DOCUMENTS

WO   WO 2016/183424 A1   11/2016

OTHER PUBLICATIONS

Enrique J. Fernandez and Pablo Artla, "Achromatic doublet intraocular lens for full aberration correction," Biomedical Optics Express 23, May 1, 2017, vol. 8, No. 5, pp. 1-9.

*Primary Examiner* — David H Willse
*Assistant Examiner* — Tiffany P Shipmon

(57) ABSTRACT

A composite light adjustable intraocular lens, can include an intraocular lens (IOL), a light adjustable lens, attached to the intraocular lens, and haptics. In some cases, a composite light adjustable intraocular lens can include an intraocular lens, and haptics, attached to the IOL with light-adjustable hinges. A method of adjusting an implanted composite light adjustable intraocular lens can include planning a targeted optical outcome of an implantation of the composite light adjustable intraocular lens into an eye; implanting, the composite light adjustable intraocular lens into the eye; performing a diagnostic measurement to evaluate an implanted optical outcome of the implantation; determining a correction based on a comparison of the planned optical outcome and the implanted optical outcome; and applying a stimulus to adjust an optical characteristic of the composite light adjustable intraocular lens to induce the determined correction.

23 Claims, 21 Drawing Sheets

(52) U.S. Cl.
CPC ...... *A61F 2210/0076* (2013.01); *G02C 7/022* (2013.01); *G02C 2202/14* (2013.01); *G02C 2202/18* (2013.01)

(58) Field of Classification Search
CPC ............ A61F 2002/1686; G02C 7/022; G02C 2202/14; G02C 2202/18
See application file for complete search history.

(56) References Cited

U.S. PATENT DOCUMENTS

| | | | |
|---|---|---|---|
| 6,231,603 B1 * | 5/2001 | Lang | A61F 2/1613 623/6.24 |
| 6,450,642 B1 | 9/2002 | Jethmalani et al. | |
| 6,695,881 B2 * | 2/2004 | Peng | A61F 2/1613 623/6.34 |
| 9,713,526 B2 | 7/2017 | Romback | |
| 2007/0002444 A1 | 1/2007 | Piers et al. | |
| 2007/0129802 A1 * | 6/2007 | Jethmalani | A61F 2/16 623/6.22 |
| 2008/0046076 A1 * | 2/2008 | Rombach | A61F 2/1632 623/6.34 |
| 2009/0015789 A1 | 1/2009 | Dai et al. | |
| 2010/0312337 A1 | 12/2010 | Zhang et al. | |
| 2010/0324674 A1 | 12/2010 | Brown | |
| 2012/0245684 A1 * | 9/2012 | Liao | A61F 2/1648 623/6.56 |
| 2015/0250583 A1 | 9/2015 | Rosen et al. | |
| 2016/0085089 A1 | 3/2016 | Hillis et al. | |
| 2016/0113761 A1 * | 4/2016 | Nishi | A61F 2/1613 623/6.13 |
| 2016/0339657 A1 | 11/2016 | Grubbs et al. | |
| 2017/0020658 A1 * | 1/2017 | Grubbs | G02B 5/208 |

* cited by examiner

COMPOSITE LIGHT ADJUSTABLE INTRAOCULAR LENS

TECHNICAL FIELD

This invention relates to light adjustable intraocular lenses, and more specifically to composite intraocular lenses that can be adjusted by illumination.

BACKGROUND

The techniques of cataract surgery have been experiencing continuous, impressive progress of late. Subsequent generations of phacoemulsification platforms and newly invented surgical lasers keep increasing the precision of the placement of intraocular lenses (IOLs) and keep reducing the unwanted medical outcomes. Also, present generations of IOLs, based on soft acrylate materials, deliver very good optical outcomes, and numerous additional medical benefits, including ease and control of the implantation process, and an advantageous haptic design.

Nevertheless, some types of challenges remain even with the latest generation of devices and IOLs. One of them is that, in spite of surgeons carrying out the most careful pre-surgical diagnostics to determine the optimal IOL to be implanted, in a notable percentage of cases the post-surgical medical outcomes, are less than optimal. This can be caused by a variety of factors, including an uneven healing process of the incisions tilting or moving the implanted IOL, or an imperfect modeling of the eye, among others.

A noteworthy breakthrough has been achieved recently by the development of lenses that can be adjusted non-invasively after the cataract surgery. These lenses involve light sensitive materials that photopolymerize upon activation by an irradiation. Irradiation with a carefully designed radial profile initiates the photopolymerization with a corresponding radial profile, which, in turn, leads to the IOL changing its physical shape and therefore, its optical power. These light adjustable lenses hold great promise to adjust and eliminate the residual post-surgical misalignments and to fine tune "the last diopter" of the IOLs post-surgically and non-invasively.

However, the present generation of these light adjustable lenses can be further improved still. Areas of possible improvements include optimized material properties that could ease the challenges of the implantation, as well as better haptic designs.

Therefore, there is an unmet medical need for intraocular lenses that deliver the advantages of both today's regular acrylate IOLs, and that of the light adjustable IOLs, while minimizing the less desirable aspects of their performance.

SUMMARY

In this patent document, the above-described needs are addressed by embodiments of a composite light adjustable intraocular lens that can include an intraocular lens (IOL); a light adjustable lens, attached to the intraocular lens; and haptics. In some cases, a composite light adjustable intraocular lens can include an intraocular lens, and haptics, attached to the IOL with light-adjustable hinges. A method of adjusting an implanted composite light adjustable intraocular lens can include planning a targeted optical outcome of an implantation of the composite light adjustable intraocular lens into an eye; implanting the composite light adjustable intraocular lens into the eye; performing a diagnostic measurement to evaluate an implanted optical outcome of the implantation; determining a correction based on a comparison of the planned optical outcome and the implanted optical outcome; and applying a stimulus to adjust an optical characteristic of the composite light adjustable intraocular lens to induce the determined correction.

DETAILED DESCRIPTION

Figure 1:
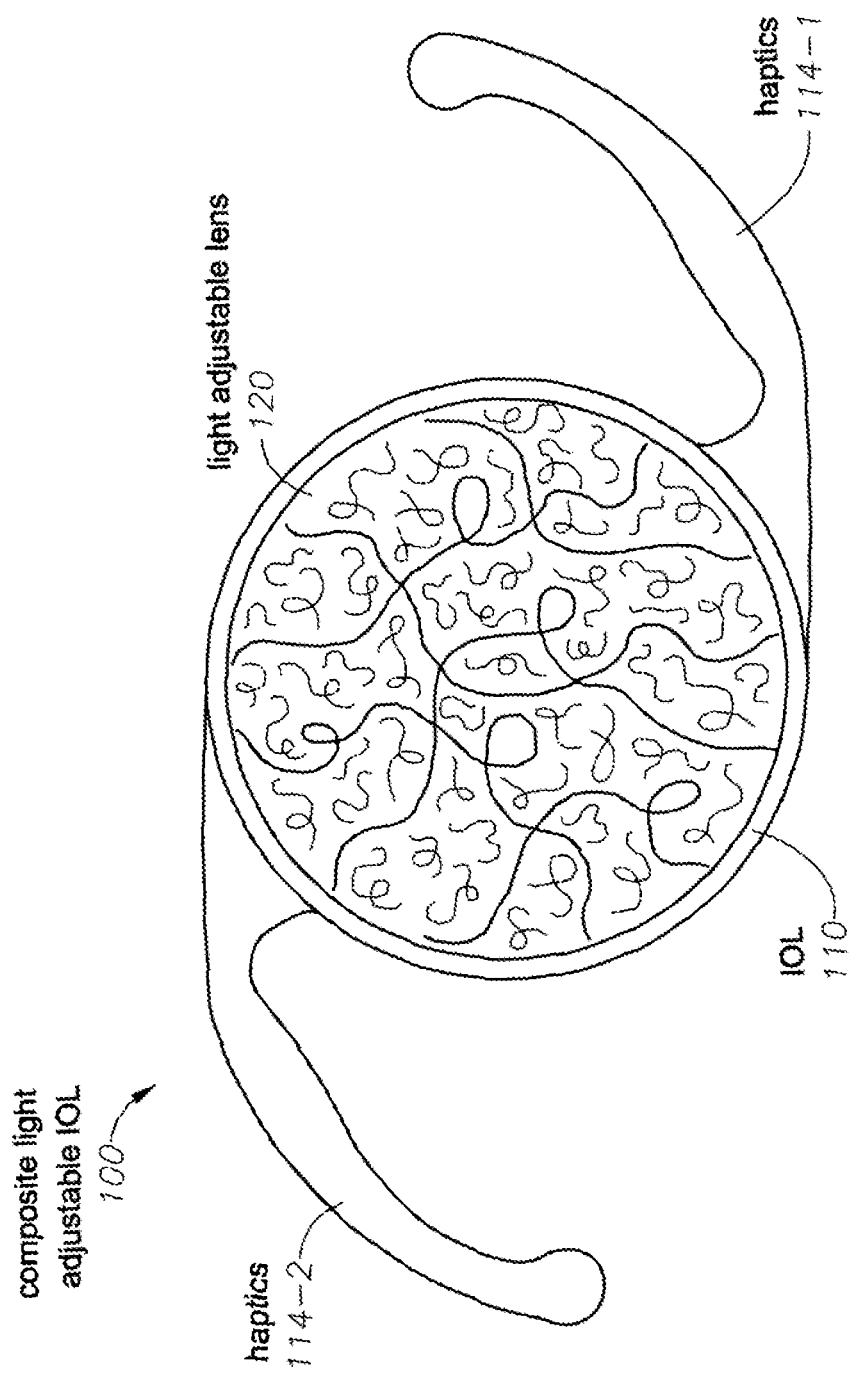
FIG. 1 illustrates a top view of a composite light adjustable IOL.

Existing light adjustable intraocular lenses are often made of silicone-based polymers, such as poly-siloxanes and corresponding copolymers. Existing non-light-adjustable intraocular lenses are often made of various acrylates. The limitations (L) and the benefits (B) of these two classes of IOLs include the followings.

(L1) The elastic constants of silicone-based IOLs are often stronger, or stiffer, than that of some other IOL's, and therefore these silicone-based IOLs are often "springy" in comparison. One consequence of this springiness is that, during the IOL implantation process, the folded silicone-based IOLs unfold quite fast as they are pushed out from the surgical inserter hand piece into the eye. This quick unfolding of the silicone-based IOLs can make the control of the insertion and the proper alignment of the silicone-based IOLs somewhat challenging for a surgeon during surgery.

(B1) in contrast, acrylate-based IOLs have softer elastic constants, and thus unfold slower during the insertion. This aspect allows the surgeon to exercise more control over the insertion of acrylate IOLs.

(L2) The design of silicone-based IOLs is often three-piece: the two haptics are often separately fabricated and subsequently inserted into the central lens body. This design feature increases manufacturing costs, may lead to a higher rate of haptics misalignment during manufacture, and to separation of the haptics from the IOL lens body during the insertion.

(B2) In contrast, some acrylate-based IOLs manage these challenges by having a one-piece design, where integrated haptics are formed from the same lens material and with the same molding step as the central lens body of the IOL. Such one-piece designs have lower manufacturing costs, deliver good haptics alignment with the lens body, and reduce the risk of haptic separation from the lens body during insertion.

At the same time, the presently known acrylate-based IOLs are not light adjustable. These non-light adjustable, often acrylate-based IOLs have drawbacks on their own. These include the followings.

(L3) When surgeons plan a cataract surgery, first they perform careful and extensive diagnostics of the cataractous eye. Based on this diagnostics, the surgeons determine the optimal placement, alignment and optical power of the IOL. However, as discussed previously, the IOLs often end up away from their planned optimal placement, possibly tilted or misaligned relative to the plan. This can happen for a variety of causes, such as uneven development of ocular tissue after the surgery.

(B3) Light adjustable IOLs offer a profound solution for this misplacement and misalignment problem. Once the IOL is implanted and settled in the capsular bag of the eye after surgery, a post-surgical diagnostics can be carried out to determine the unintended shifts in alignment and placement of the implanted IOL. The results of this post-surgical diagnostics can be used to determine what corrections of the IOL can compensate the misplacement and the misalignment of the implanted IOL. This post-surgical determination can be used to perform a light adjustment procedure to bring about the determined IOL corrections in the implanted light adjustable IOL.

(L4) The above misalignment problem is particularly acute for toric IOLs, where the implantation targets the elimination of a cylinder in the eye. For toric IOLs, an unintended rotation of the toric IOL axis by only 10 degrees after implantation can cause about 30% loss of efficiency. E.g. a nominal 3D cylinder of a toric IOL can be reduced to an effective 2D cylinder if the cylinder axis ends up rotated by only 10 degrees during or after implantation.

(B4) Light adjustable IOLs can be implanted without any preformed toric cylinder. After the implantation, when the IOL settled and stopped its unintended rotation, the surgeon can apply an illumination to form a cylinder in the settled IOL, with its axis oriented exactly in the planned or targeted direction. Thus, light adjustable IOLs are capable of avoiding the possible loss of efficiency induced by unintended misalignments of the cylinder axis of toric IOLs.

This document describes intraocular lenses that combine the benefits (B1)-(B4) of the above two classes of IOLs, and therefore have the potential to overcome and to avoid the limitations (L1)-(L4) each class of IOLs has on their own. Additional benefits of various embodiments will be also articulated below.

FIG. 1 illustrates a top view of a composite light adjustable intraocular lens 100 that includes an intraocular lens (IOL) 110, a light adjustable lens (LAL) 120, attached to the intraocular lens 110; and haptics 114-1 and 114-2, cumulatively also referred to as haptics 114. The haptics 114 can include various number of haptic arms. Embodiments with one, two, three and more haptic arms all have their advantages. For compactness and specificity, the rest of the description is directed to composite light adjustable intraocular lenses 100 with two haptic arms 114-1 and 114-2, but embodiments with other number of haptic arms are understood to be within the scope of the overall description.

Figure 2A:
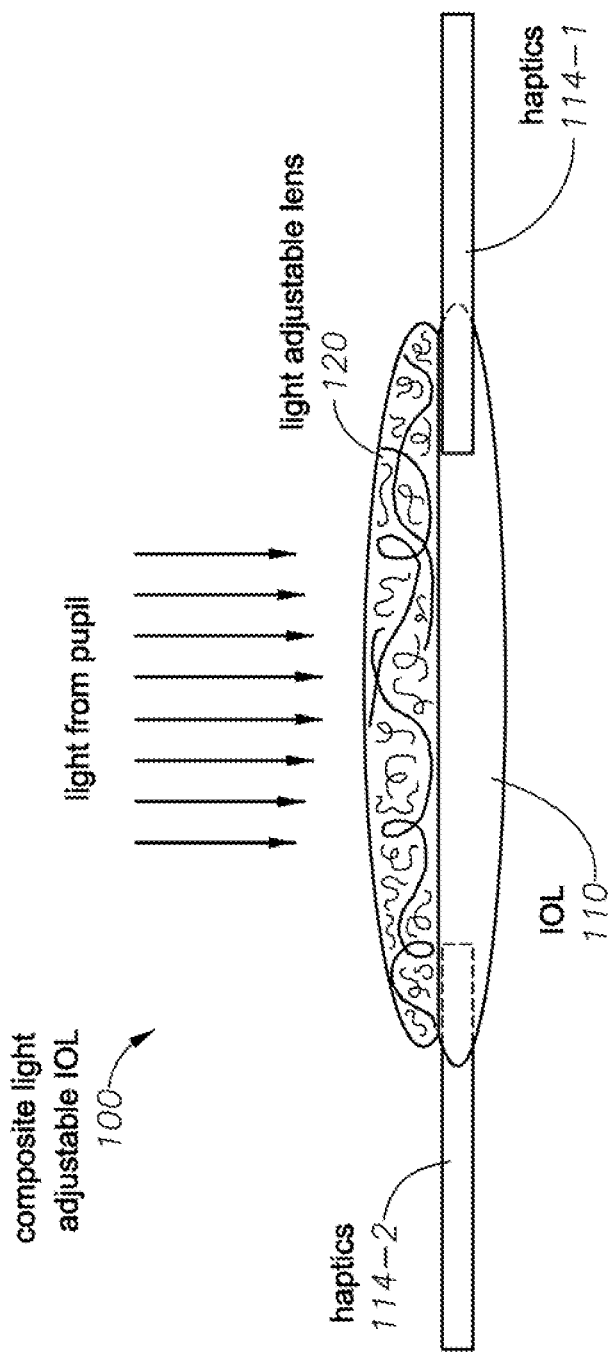
FIGS. 2A-C illustrate side views of embodiments of a composite light adjustable IOL, or CLA IOL.
Figure 2B:
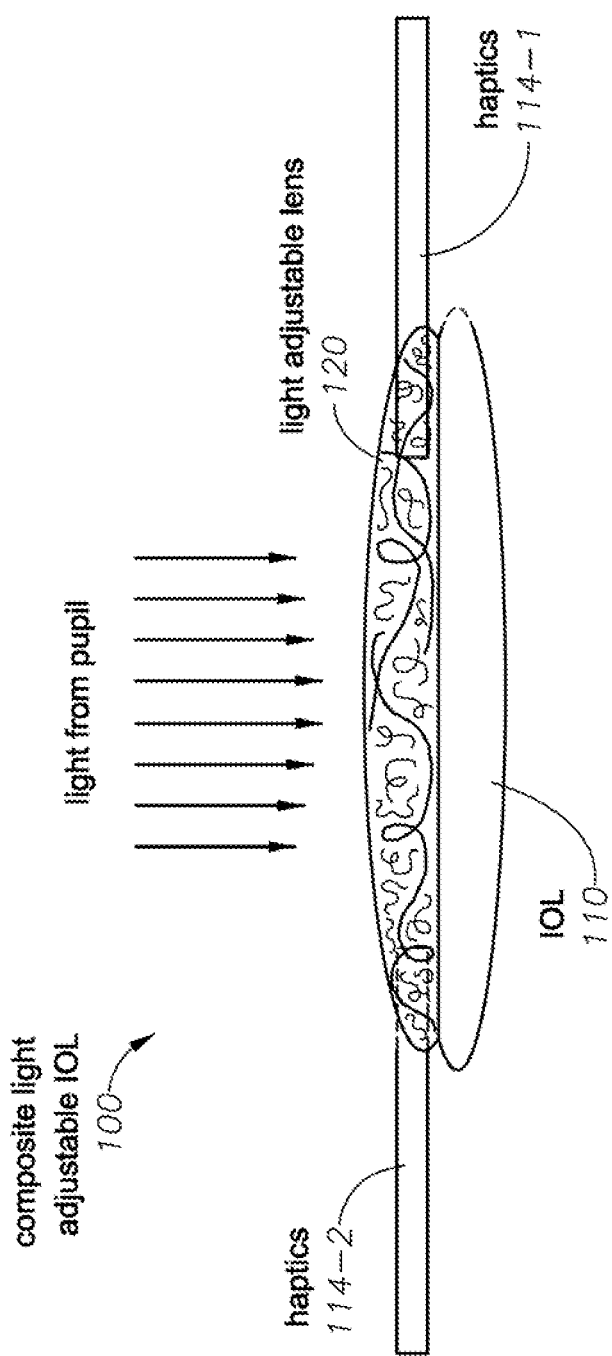
Figure 2C:
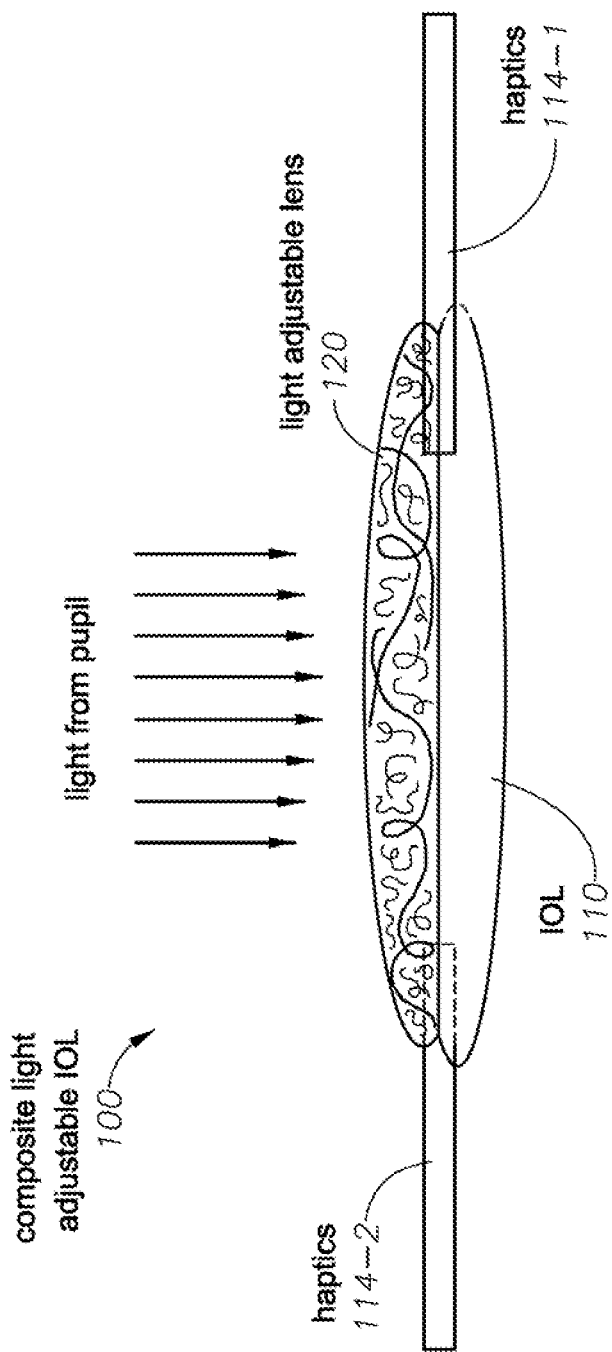

FIGS. 2A-C and FIG. 3 illustrate side views of embodiments of the composite light adjustable intraocular lens 100, or CLA IOL 100. FIGS. 2A-C illustrate a CLA IOL 100 where the light adjustable lens 120 can be attached to the IOL 110 at a proximal surface of the IOL 110. In this document, the terms "proximal" and "distal" are used in relation to the light incident from the pupil of the eye. Proximal indicates a position that is closer to the pupil. The shown embodiments differ in the manner the haptics 114-1 and 114-2, again, cumulatively haptics 114, are attached to the components of the CLA IOL 100.

FIG. 2A illustrates a CLA IOL 100, where the haptics 114 are attached to the IOL 110. For example, the haptics 114 can be molded together with the IOL 110, as is the case with many acrylic or acrylate IOLs, described above. These haptics 114 can be made of the same acrylic material as the IOL 110 itself, and can be molded in the same, single step as the IOL 110 itself. As described earlier, such integrated haptics 114 are easier to manufacture, are more reliably aligned with the IOL 110 and are less likely to separate from the IOL 110 during insertion.

FIG. 2B illustrates a CLA IOL 100 where the haptics 110 are attached to the light adjustable lens 120. Finally, FIG. 2C illustrates a CLA IOL 100 where the haptics 114 are attached to both the IOL 110 and the light adjustable lens 120 in a shared manner.

Figure 3:
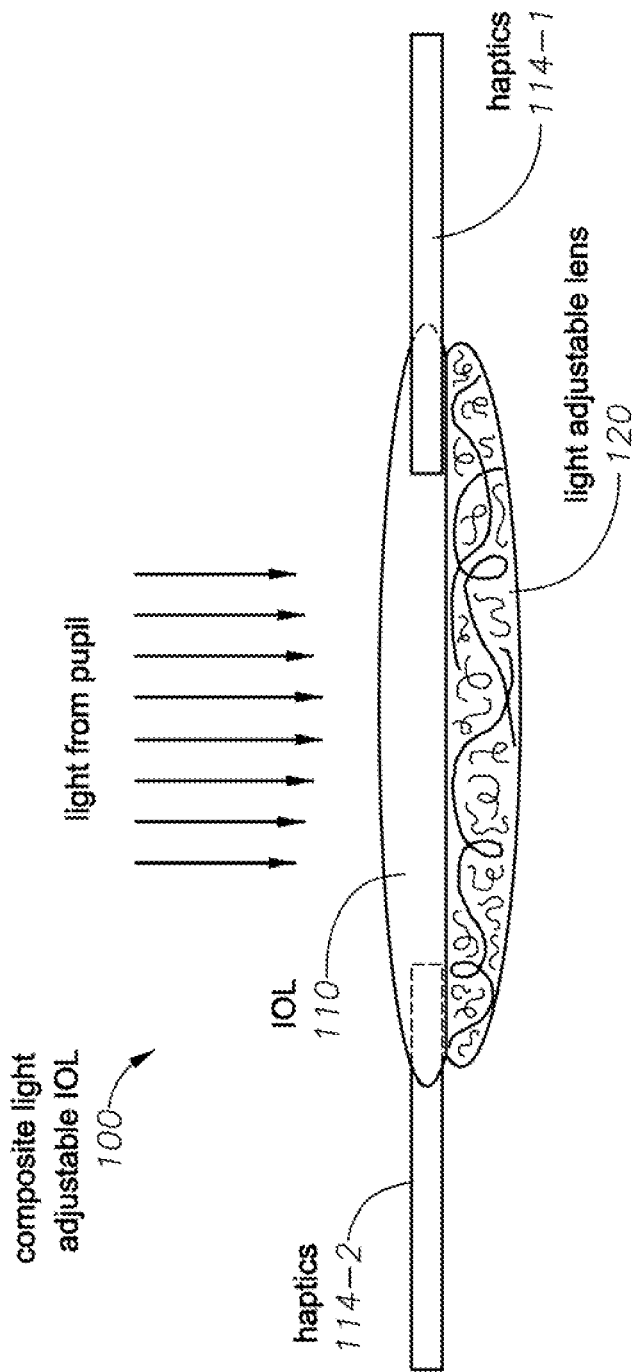
FIG. 3 illustrates a side view of another embodiment of a composite light adjustable IOL.

FIG. 3 illustrates a CLA IOL 100, where the light adjustable lens 120 can be attached to the IOL 110 at a distal surface of the IOL 110. The light adjustable lens 120—IOL 110 sequence of FIGS. 2A-C, and the IOL 110—light adjustable lens 120 sequence of FIG. 3 can both have their own advantages.

In some embodiments, the IOL 110 can be designed, or selected, to deliver the majority, or the entirety, of the intended optical power of the CLA IOL 100. In such embodiments, the light adjustable lens 120 can be designed only to provide the corrections and adjustments the surgeon anticipates may become necessary after the CLA IOL 100 settles in the eye with some unintended misalignment. Since the role of the light adjustable lens 120 in such embodiments is only to provide a correction of 1D-2D of optical power or cylinder, it can be a much thinner lens than in non-composite light adjustable IOLs, where all the optical power is generated by the light adjustable material. The CLA IOL embodiments that include only a corrective light adjustable lens 120 can therefore involve a much thinner light adjustable lens 120. The adjustment and lock-in of the light adjustable lens 120 in such a CLA IOL 100, described in relation to FIG. 4, therefore may require a smaller irradiation power, thereby increasing the safety of the overall light adjustment procedure.

The light adjustable lens 120 can be designed to provide a vision correction up to 2D, in other embodiments, only up to 1D. In some embodiments, either the IOL 110, or the light adjustable lens 120 can be a meniscus lens.

Concerning the chemical composition, in acrylate embodiments, the IOL 110 can include a monomer, a macromer, or a polymer, any one of which can include an acrylate, an alkyl acrylate, an aryl acrylate, a substituted aryl acrylate, a substituted alkyl acrylate, a vinyl, or copolymers combining alkyl acrylates and aryl acrylates. In some IOL 110$s$, the alkyl acrylate can include a methyl acrylate, an ethyl acrylate, a phenyl acrylate, or polymers and copolymers thereof.

In some embodiments, the chemical composition of the IOL 110 can, include a fractional mixing of the chemical composition of the light adjustable lens 120. Such an IOL 110 can include silicone-based monomers or macromers, forming polymers or copolymers with the acrylate, alkyl acrylate, an aryl acrylate, a substituted aryl acrylate, a substituted alkyl acrylate, a vinyl, or copolymers combining alkyl acrylates and aryl acrylates.

In some embodiments, a monomer, a macromer, or a polymer of the IOL 110 can have a functional croup that can include a hydroxy, amino, vinyl, mercapto, isocyanate, nitrile, carboxyl, or hydride. The functional group can be cationic, anionic or neutral.

In some embodiments, the light adjustable lens 120 can include a first polymer matrix, and a refraction modulating composition, dispersed in the first polymer matrix, wherein the refraction modulating composition is capable of a stimulus-induced polymerization that modulates a refraction of the light adjustable lens 120. The first polymer matrix can include a siloxane based polymer, formed from macromer and monomer building blocks with an alkyl group, or an aryl group.

In some embodiments of the composite light adjustable intraocular lens 100, the first polymer matrix can include a fractional mixing of at least one of an acrylate, an alkyl acrylate, an aryl acrylate, a substituted aryl acrylate, a substituted alkyl acrylate, a vinyl, and copolymers combining alkyl acrylates and aryl acrylates. These can form at least one of polymers and copolymers with compounds of the first polymer matrix.

The above embodiments, where the IOL 110 includes a fractional mixing of a material of the light adjustable lens 120, and where the light adjustable lens 120 includes a fractional mixing of a material of the IOL 110, can be formed to increase the compatibility of the materials of the lenses 110 and 120, thereby increasing the mechanical, physical and chemical robustness of the CLA IOL 100.

Embodiments of the light adjustable lens 120 can also include a photoinitiator, to absorb a refraction modulating illumination; to be activated upon the absorption of the illumination; and to initiate the polymerization of the refraction modulating compound. In some embodiments, the photoinitiator of the light adjustable intraocular lens 120 can also include an ultraviolet-absorber.

Embodiments of light adjustable lenses 120 have been described in substantial detail in the commonly owned U.S. Pat. No. 6,450,642, to J. M. Jethmalani et al., entitled: "Lenses capable of post-fabrication power modification", hereby incorporated in its entirety by reference.

Figure 4:
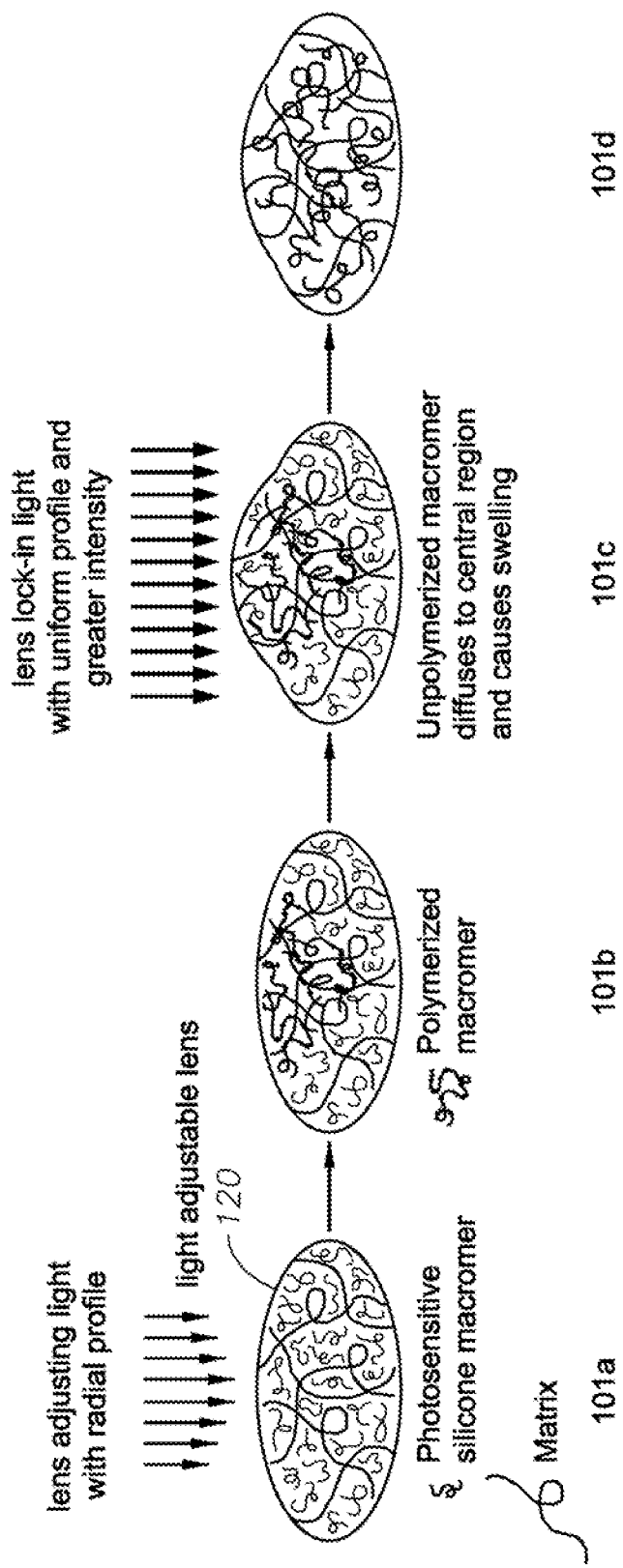
FIG. 4 illustrates steps of a light adjustment procedure.

FIG. 4 illustrates four steps 101a-101d of a process of modifying a refraction property of the light adjustable lens 120 by illumination. Very briefly, in step 101a, the light adjustable lens 120 that includes a matrix and within it photosensitive macromers made from suitable materials, such as silicones, is illuminated by a lens adjusting light with a radial profile.

In step 101b, the exposure to the adjusting light causes the photosensitive macromers to polymerize with a radial profile, determined by the radial profile of the adjusting light.

In step 101c, the unpolymerized macromers diffuse to the central region where the photosensitive macromers photopolymerized previously. This causes a swelling of the light adjustable lens 120 in this central region. (In complementary processes, where the radial profile of the illuminating light in more intense towards the peripheral annulus of the light adjustable lens 120, the unpolymerized macromers diffuse outward to the peripheral annulus, causing the swelling of this peripheral annulus.)

Still in step 101c, the swelling can be followed by applying a lock-in light with an essentially uniform radial profile and greater intensity to polymerize all remaining macromers. In step 101d, this lock-in causes the light adjustable lens 120 to reach and to stabilize a shape that is swollen in its center, and therefore has a light-adjusted optical power. The above is only a very brief summary of the light adjustable lenses and their light adjustment procedure. A much more detailed explanation is provided in the incorporated U.S. Pat. No. 6,450,642, to J. M. Jethmalani et al.

In some embodiments, the IOL 110 and the light adjustable lens 120 are adapted to retain a chemical separation even after they are attached. This chemical separation can be achieved, e.g., by employing a refraction modulating composition in the light adjustable lens 120 that is not soluble in the materials of the IOL 110, and thus it does not diffuse into the IOL 110 from the light adjustable lens 120, in spite of the mobility of its constituent macromers in the first polymer matrix of the light adjustable lens 120 itself.

As mentioned before, one of the advantages of combining the IOL 110 that can be acrylic-based, with the light adjustable lens 120 that can be silicone-based is that an elastic constant of an acrylic IOL 110 can be softer than a corresponding elastic constant of a silicone light adjustable lens 120. In a CLA IOL 100, where the IOL 110 is considerably softer than the light adjustable lens 120, the "springiness" of the overall CLA IOL 100 can be considerably reduced relative to that of the light adjustable lens 120 alone. Such a CLA IOL 100 can be inserted with substantially improved control and predictability during cataract surgery, thus improving the surgical outcome.

As described in relation to FIG. 4, in some embodiments, the refraction properties of the light adjustable lens 120 are modified by applying an ultraviolet (UV) illumination. Safety considerations dictate that the applied UV illumination shall be prevented from reaching the retina of the eye, or at least the intensity of its transmitted component greatly attenuated. To this end, some embodiments of the CLA IOL 100 may contain UV absorbers. There are several different designs for including a UV absorber.

Figure 5:
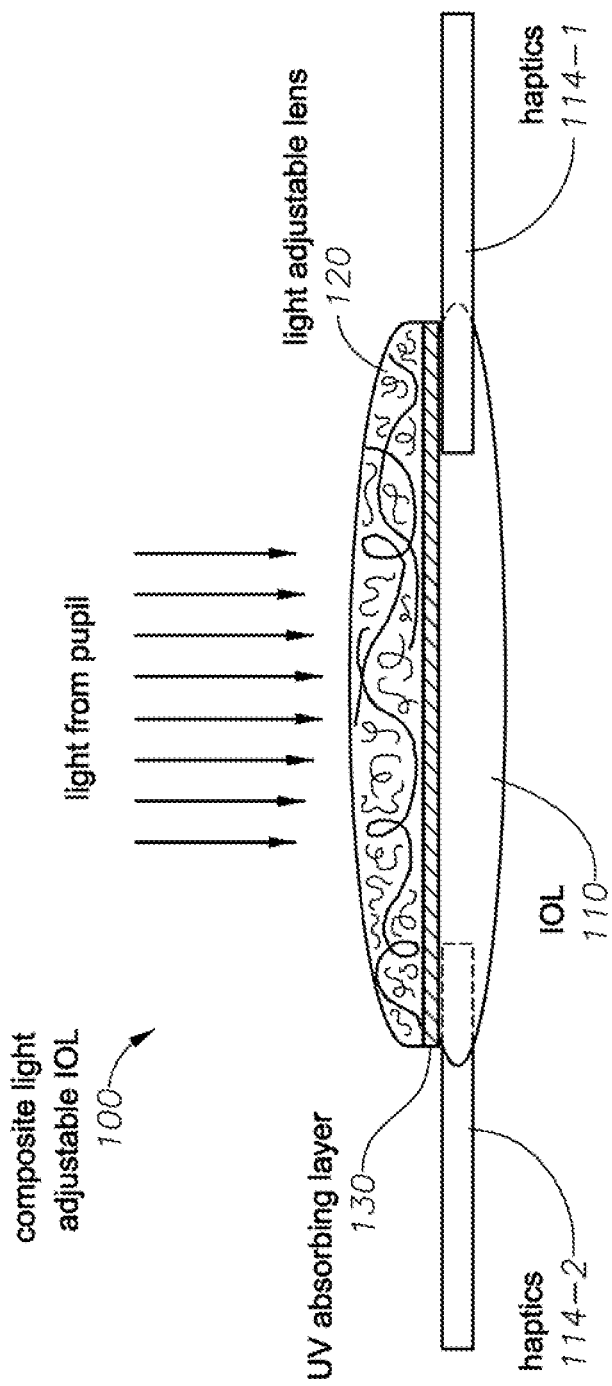
FIG. 5 illustrates an embodiment of a composite light adjustable IOL with a UV absorber layer.

In some embodiments, the UV absorber can be related to the light adjustable lens 120. FIG. 5 illustrates that in some designs, an ultraviolet absorbing layer 130 can be formed at a distal surface of the light adjustable lens 120. In other embodiments, an ultraviolet absorbing material can be dispersed throughout the light adjustable lens 120.

In other designs, the UV absorber can be related to the IOL 110. Since the UV light needs to reach the light adjustable lens 120 for the adjustment procedure, in such embodiments the light adjustable lens 120 can be attached to the IOL 110 at a proximal surface of the IOL 110, so that the UV absorber in the IOL 110 does not block the UV illumination from reaching the light adjustable lens 120. With such an arrangement, in some embodiments, an ultraviolet absorbing material can be dispersed throughout the IOL 110; in others, the CLA IOL 100 can include the ultraviolet absorbing layer 130. This ultraviolet absorbing layer 130 can be on a proximal or on a distal surface of the IOL 110, since either of these designs still places the ultraviolet absorbing layer 130 distal to the light adjustable lens 120.

In embodiments of the composite light adjustable intraocular lens 100, the light adjustable lens 120 can be attached to the IOL 110 by a variety of designs. In some cases, the light adjustable lens 120 can be attached to the IOL 110 by a chemical reaction, a thermal treatment, an illumination treatment, a polymerization process, a molding step, a curing step, a lathing step, a cryo-lathing step, a mechanical process, an application of an adhesive, or by any combination of these methods.

Figure 6:
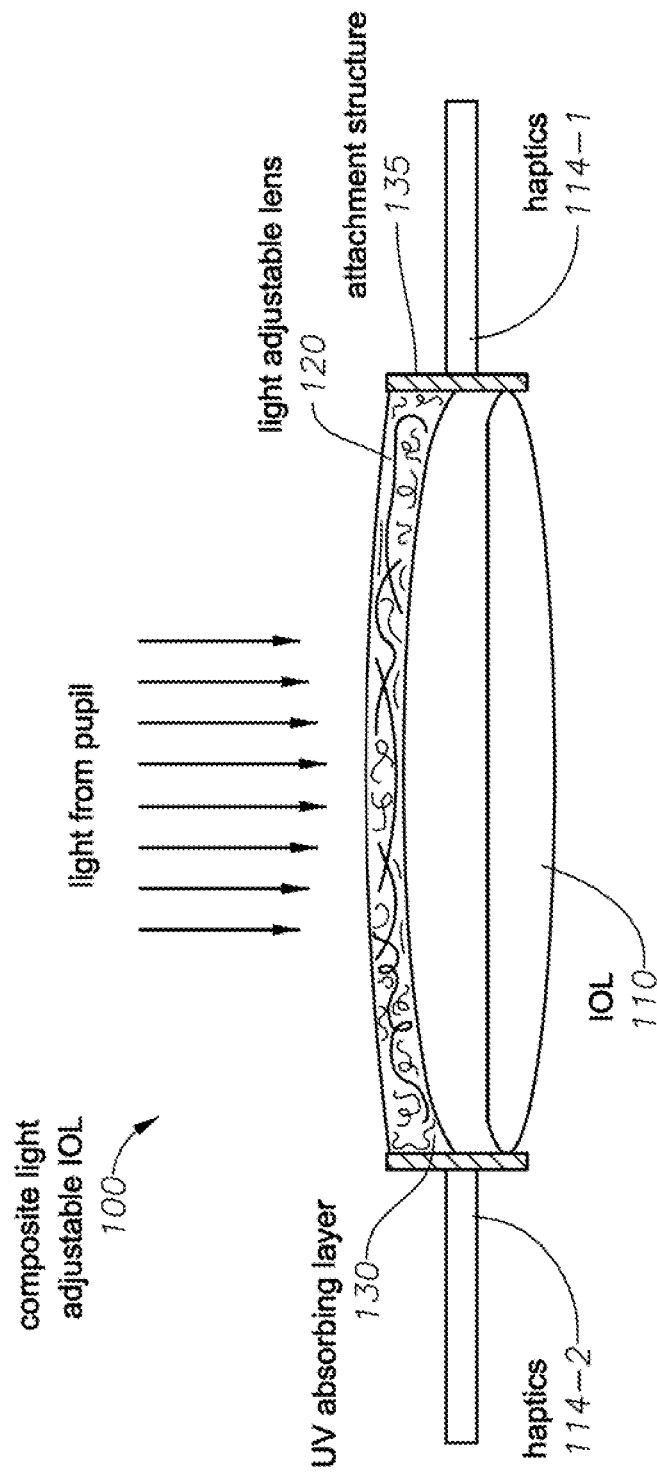
FIG. 6 illustrates a CLA IOL with an attachment structure.

FIG. 6 illustrates that some embodiments of the CLA IOL 100 can include an attachment structure 135 for attaching the light adjustable lens 120 to the IOL 110. This attachment structure 135 can include a cylinder, a ring, an open tub, into which an optical element can be inserted, or a clasp, among others. Such structures can have multiple advantages.

(a) For example, CLA IOLs 100 with an attachment structure 135 can be modular. This can be advantageous for pre-operative purposes, as a surgeon may need to keep a much smaller inventory. Once pre-operative diagnostics determines what IOL 110 needs to be paired with light adjustable lens 120, the surgeon can select a separately stored IOL 110, and a separately stored light adjustable lens 120, and assemble the CLA IOL 100 by inserting the two selected lenses into the attachment structure 135.

(b) The modularity can be advantageous post-operatively as well. If at the end of the cataract surgery it is determined that for whatever reason, the IOL 110 was not selected optimally, if a non-modular CLA IOL 100 was used, then the surgeon needs to reopen the eye and remove the entire implanted CLA IOL 100, including its extended haptics 114. Such a full-IOL removal can pose substantial challenges and can lead to undesirable medical outcomes, such as broken haptic pieces.

In contrast, if a modular CLA IOL 100 was implanted, then, upon the reopening of the eye the surgeon does not need to remove the entire CLA IOL 100, only the non-optimal IOL 110, and exchange it with a better selected IOL 110. This procedure avoids the need to remove the entire CLA IOL 100, and thus reduces the risk of undesirable medical outcomes. Also, typically such replacement procedures may need a shorter incision, since only parts of the IOL are being replaced: another medical benefit.

(c) Finally, IOLs with taller structures have benefits in the context of reducing Posterior Capsule Opacification, or PCO. This will be described below in more detail in relation to FIGS. 12A-B. A CLA IOL 100 with an attachment structure 135 can be made as tall as desired by the surgeon.

In embodiments of the CLA IOL 100, the IOL 110 an be an advanced and complex IOL, such as a multifocal IOL, an aspheric IOL, a toric IOL, or a diffractive IOL. Such advanced IOLs offer vision corrections beyond the correction of the optical power alone. They can help reducing presbyopia, astigmatism, cylinder, or other types of aberrations. However, the performance of these advanced IOLs requires the placement of the IOL with higher than usual precision. If the implanted IOL, ends up misplaced, or misaligned, at the end of cataract surgery or later, the vision improvements and benefits can be substantially inferior relative to the outcomes promised to the patient. The fact that such unintended misalignments and rotations happen in a notable percent of cataract surgeries is a key factor limiting the wider market acceptance of such advanced IOLs.

In contrast, if a CLA IOL 100 gets misplaced, misaligned, or rotated relative to the planned location, angle, or direction in the eye, the light adjustable lens 120 of the CLA IOL 100 can be adjusted to compensate this misalignment, or rotation. Therefore, CLA IOLs 100 have the potential to deliver the promised vision improvements to the patients reliably. This benefit of the CLA IOLs 100 can start a fast expansion of the market acceptance and the market share of the advanced IOLs.

In some other embodiments, the insertion of the embodiments of FIG. 6 can be eased by making the attachment structure 135 a fluid-fillable structure instead of a hard structure. Such a fluid-fillable attachment structure 135 can be inserted into the eye in its unfilled form and then filled up with liquid only after insertion. In some embodiments, a UV absorbing layer 130 can be provided at the distal surface of the light adjustable lens 120.

FIGS. 7A-C, FIGS. 8A-C and FIG. 9 illustrate the above general considerations on a CLA IOL 100 that includes a toric IOL 110, aimed at correcting a cylinder in an eye.

Figures 7A, 7B, 7C:
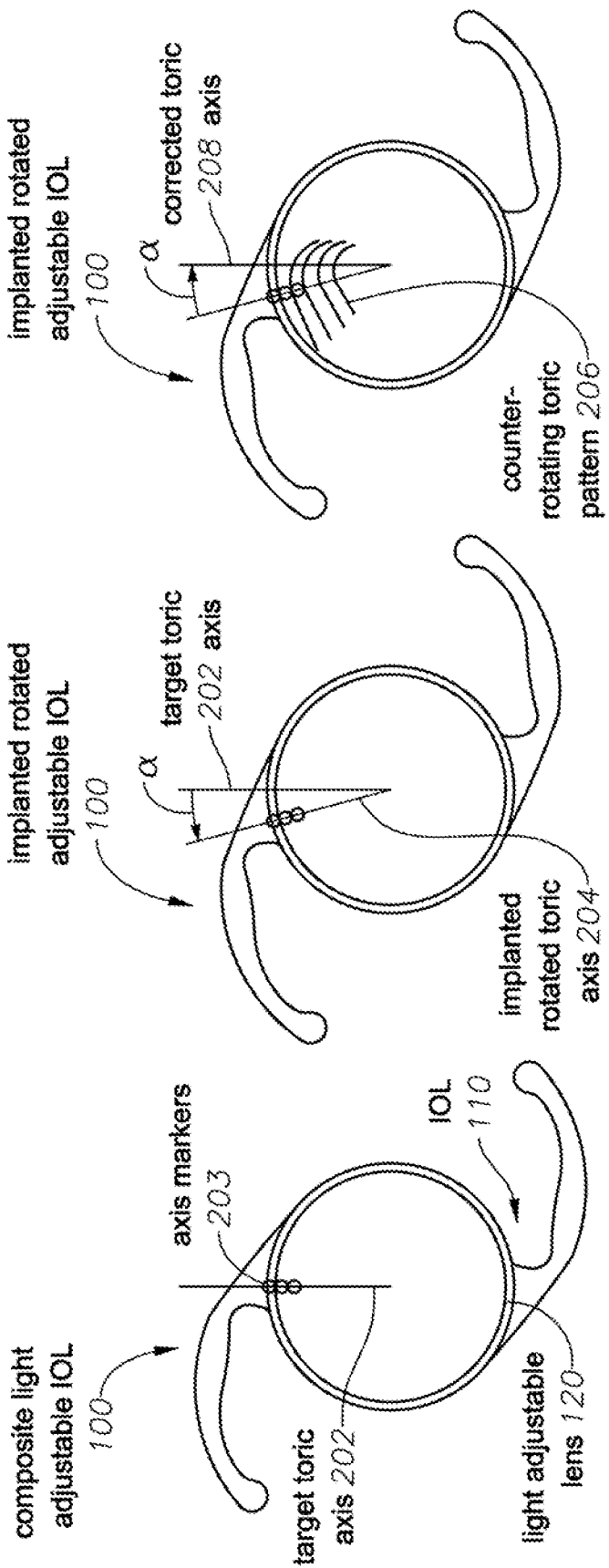
FIGS. 7A-C illustrate a formation of a counter-rotating toric pattern in an implanted rotated toric CLA IOL.

FIG. 7A illustrates a surgical situation where, to compensate a cylinder in an eye, a surgeon decided to implant a CLA IOL 100 with a toric IOL 110, whose target toric axis 202 was planned to be oriented in the indicated direction—for simplicity and clarity, chosen as straight up in the plane of FIG. 7A. Tonic IOLs often include axis markers 203 to indicate the direction of the toric axis for the surgeon.

FIG. 7B illustrates that, after the end of the cataract surgery and the closing of the incisions, the implanted CLA IOL 100 may have rotated for a variety of reasons, so that the implanted rotated toric axis 204 of the implanted CLA IOL 100 makes an unintended rotational angle $\alpha$ with the target toric axis 202.

FIG. 7C illustrates that the surgeon can devise and carry out an illumination procedure on the light adjustable lens 120 of the CLA IOL 100 to form a counter-rotating toric pattern 206, thereby causing a counter-rotation of the overall toric axis, so that the corrected toric axis 208 after the light adjustment procedure ends up pointing in the same direction as the originally planned target toric axis 202.

Figure 8A:
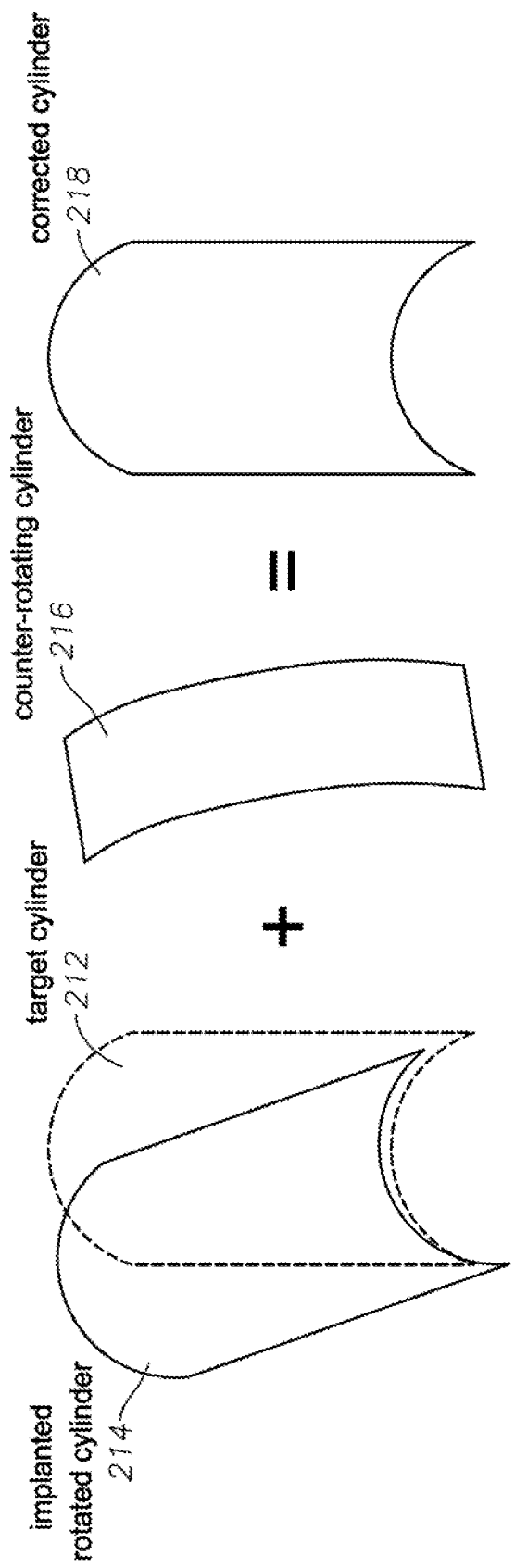
FIGS. 8A-C illustrate the formation of an analogous counter-rotating cylinder using a vector formulation.

FIG. 8A illustrates the same procedure on the level of the cylinder patterns 212-218. The surgeon in the pre-surgical planning phase of the cataract surgery may have decided that the cylinder vision problem of the patient shall be cured by implanting a CLA IOL 100 with a toric IOL 110, that has a target cylinder pattern 212, oriented as shown. However, after the implantation, the CLA IOL 100 may have unintentionally rotated to an implanted rotated cylinder 214. Such a misaligned, rotated cylinder 214 provides a much-reduced vision improvement, as explained previously. As the rotational angle grows, the implanted rotated cylinder 214 can even turn into a net negative effect, being more a nuisance and disorientation than a benefit for the patient.

To compensate this unwanted medical outcome, the surgeon can carry out a post-surgical diagnostic procedure to determine a corrective counter-rotating cylinder 216, the implementation of which can correct the unintended and unwanted rotation of the CLA IOL 100. As shown, the surgeon can perform a light adjustment procedure of the light adjustable lens 120 of the CLA IOL 100 in order to create the counter-rotating cylinder 216 in the light adjustable lens 120. The superposition of the implanted rotated cylinder 214 and the counter-rotating cylinder 216 can sum up into a shape of the light adjustable lens having a corrected cylinder 218, whose direction is aligned with the direction of the originally planned target cylinder 212. These steps are analogous to the steps of FIGS. 7A-C, described previously.

Figure 8B:
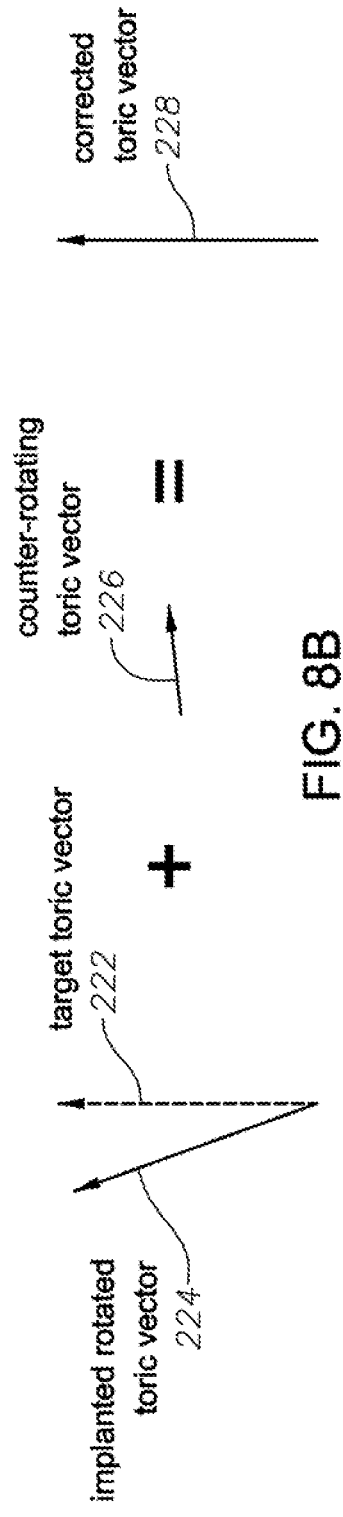

FIG. 8B illustrates the same procedure in a geometric language, where the cylinder patterns are represented by corresponding vectors. The directions of the vectors are indicative of the directions of the represented cylinders, and the magnitudes of the vectors can represent the strength, curvature, or diopters of the cylinders. The target toric vector 222 represents the target cylinder 212, and the implanted rotated toric vector 224 represents the implanted rotated cylinder 214 of the CLA IOL 100 after implantation. As before, the surgeon post-operatively can determine the counter-rotating toric vector 226, representing the counter-rotating cylinder 216, necessary to correct the unintended post-surgical rotation of the toric IOL 110. When the surgeon performs the light adjustment procedure to adjust the light adjustable lens with the counter-rotating toric vector 226, the superposition of the implanted rotated toric vector 224 and the counter-rotating toric vector 226 restores the corrected toric vector 228 to have the same direction and magnitude as the target toric vector 222.

Figure 8C:
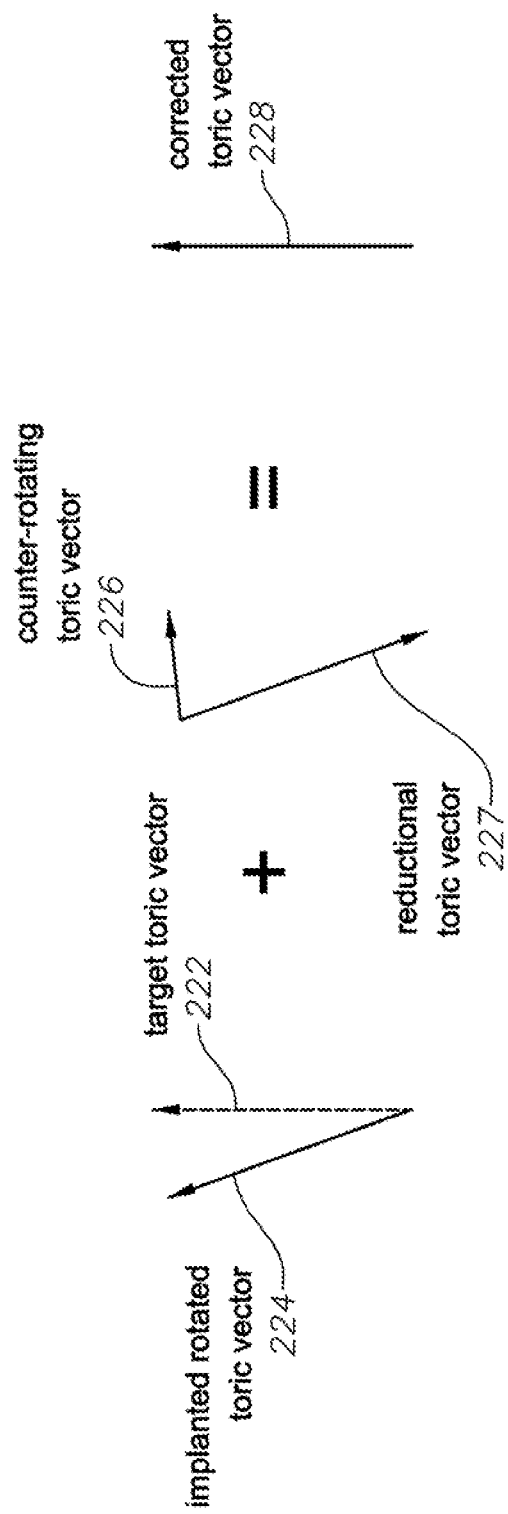

FIG. 8C illustrates in the language of the vector representation that there can be different ways to bring about the necessary correction. For example, the correctional pattern can include a reductional toric vector 227 that reduces, or even eliminates, the implanted rotated toxic vector 224. The counter-rotating toric vector 226 can then be chosen, to rotate the remaining portion of vector 224 (that is equal to the sum of the vectors 224 and 227 into the corrected toric vector 228.

In a demonstrative example, in an embodiment of the CLA IOL 100 that includes a toric IOL 110 for correcting a cylinder greater than 2D, the light adjustable lens 120 can be adapted to be able to correct a cylinder up to 2D. For example, if the toric IOL 110 was intended to correct a 6D cylinder, but the toric axis was rotated by 10 degrees, this translates into a 30% reduction of efficiency, as described earlier, providing a net 4D cylinder improvement for the patient. However, the surgeon can perform a light adjustment procedure on the light adjustable lens 120 to correct the 2D cylinder that was lost to the unintended rotation, thereby restoring the full 6D cylinder promised to the patient.

Figure 9:
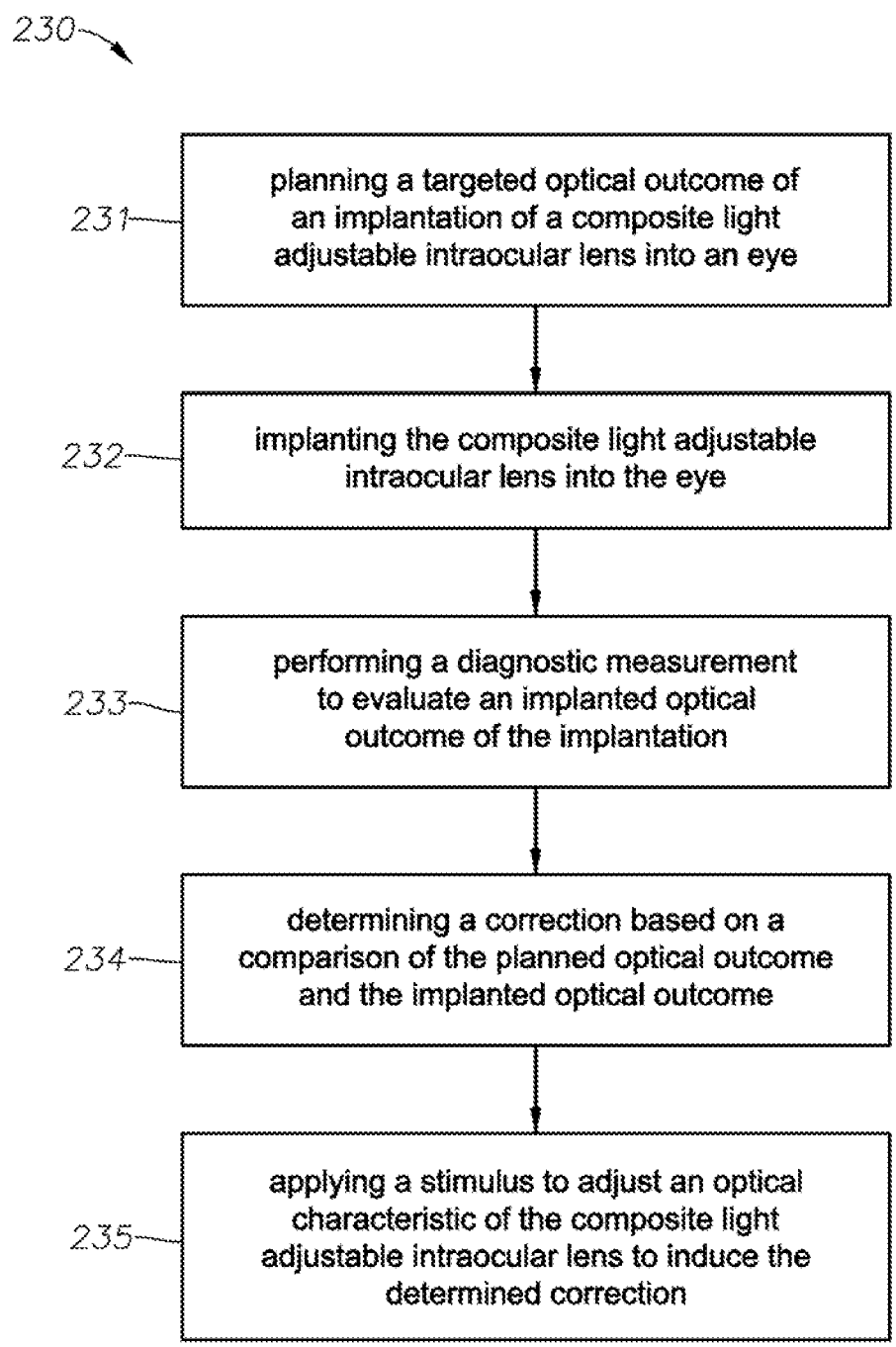
FIG. 9 illustrates a method of adjusting a composite light adjustable IOL.

FIG. 9 illustrates the steps of a corresponding method 230 of adjusting an implanted composite light adjustable intraocular lens 100 in more general terms. The method 230 can include the following, steps.

231—Planning a targeted optical outcome of an implantation of a composite light adjustable intraocular lens into an eye.

232—implanting the composite light adjustable intraocular lens into the eye.

233—Performing a diagnostic measurement to evaluate air implanted optical outcome of the implantation.

234—Determining a correction based on a comparison of the planner optical outcome and the implanted optical outcome.

235—Applying a stimulus to adjust an optical characteristic of the composite light adjustable intraocular lens to induce the determined correction.

In the procedure described in relation to FIGS. 7A-C and FIGS. 8A-C, the method 230 can be adapted for a case where the targeted optical outcome is the target cylinder 202/212/222; the implanted optical outcome is an implanted rotated cylinder 204/214/224; and the determined correction is a counter-rotating cylinder 206/216/226. These steps can adjust the implanted rotated cylinder 204/214/224 into the corrected cylinder 208/218/228, that is closely related to the target cylinder 202/212/222.

Figure 10A:
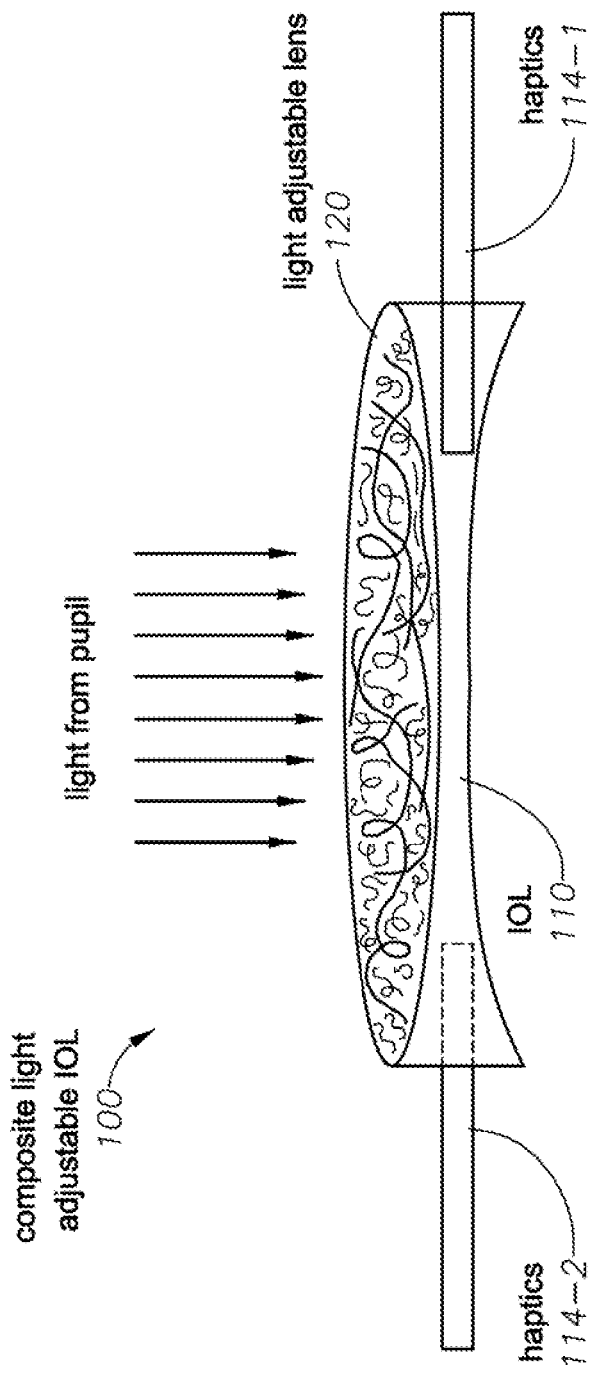
FIGS. 10A-B illustrate chromatic aberration-reducing CLA IOLs.
Figure 10B:
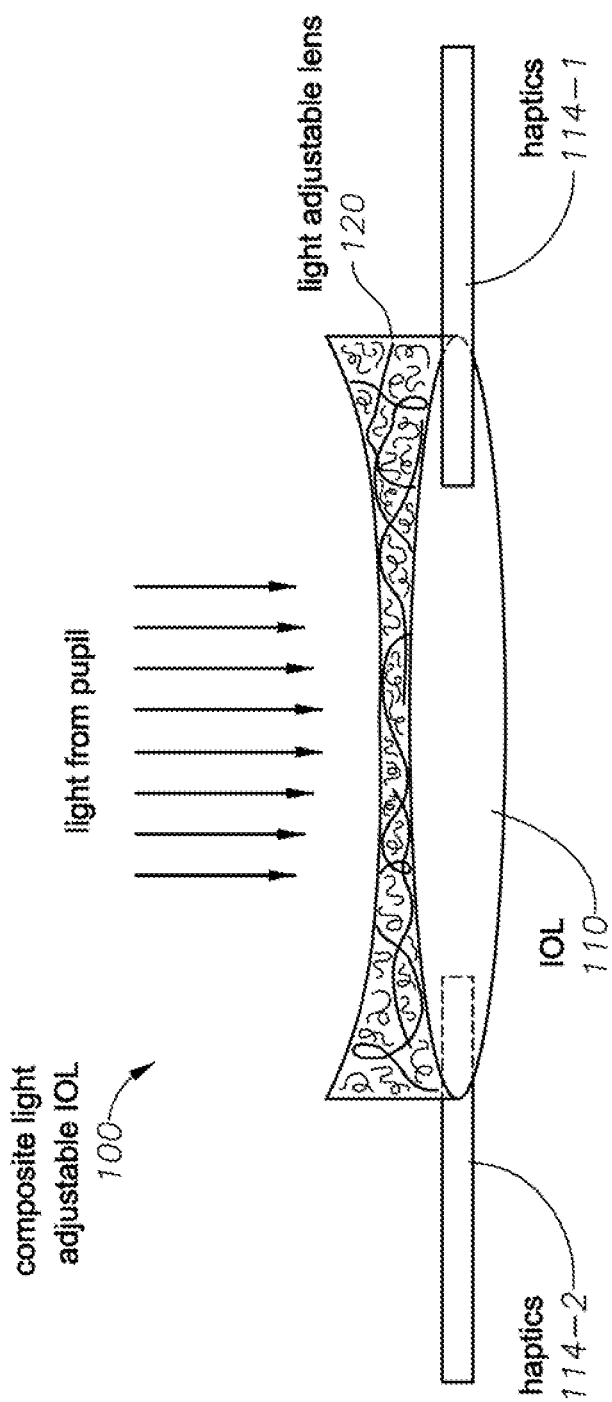
Figure 11:
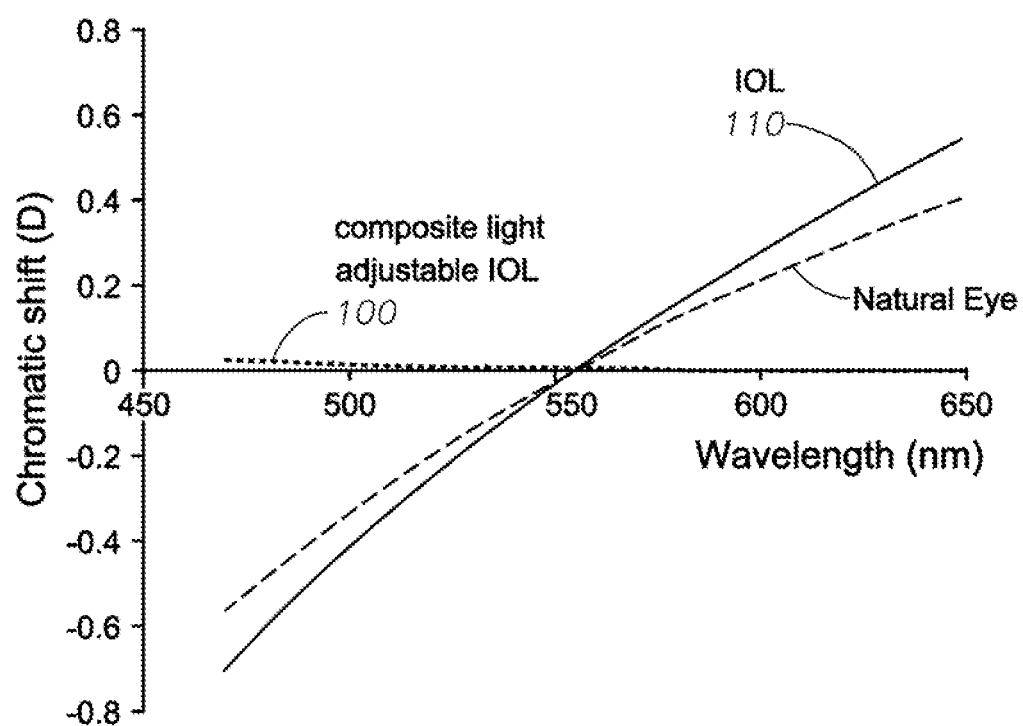
FIG. 11 illustrates the chromatic shift of a CLA IOL, in comparison to a regular IOL.

Next, FIGS. 10-11 illustrate an embodiment of the CLA IOL 100 that provides the additional medical benefit of chromatic aberration reduction. This embodiment is developed starting from the observation that the optical system of the eye, its main constituents being the cornea and the lens, exhibits a chromatic dispersion, as the effective index of refraction $n_e$ of the involved eye tissues depend on the wavelength of the light: $n_e = n_e(\lambda)$. It has been found that the derivative of $n_e(\lambda)$ is typically negative: $\partial n_e/\partial \lambda < 0$. Therefore, the optical power $P_e$ of the eye, proportional to $(n_e - 1)$, also has a negative derivative with respect to the wavelength: $\partial P_e/\partial \lambda < 0$. Even for healthy persons with 20/20 vision, this chromatic dispersion of the eye tissues causes the short wavelength ("blue") components of an image focused and imaged proximal the retina, while the long wavelength ("red") components focused distal to the retina, thereby causing some degree of blurring and image quality deterioration. This blurring of the color-components of the image is often referred to as chromatic aberration.

Our brain learned to accept a limited degree of this chromatic aberration. Nevertheless, cataract surgery has the opportunity to provide an additional medical benefit by implanting chromatic aberration-compensating IOLs that compensate the eye's own chromatic aberration and image all wavelength components to the retina, thereby reducing the chromatic aberration and sharpening the vision.

The dependence of the index of refraction on the wavelength is often characterized by the Abbe number, defined as $V = (n_D - 1)/(n_F - n_C)$, where $n_D$, $n_F$, and $n_C$ are the indices of refraction at the Fraunhofer D, F, and C spectral lines at 589, 486, and 656 nm, respectively. Most Abbe numbers are in the 20-90 range. For conical and lens tissue, the Abbe number is in the 50-60 range. The optical power $P_I$ of the intraocular lens depends on the index of refraction $n_I(\lambda)$ through the lensmaker's equation: $P_I = (n_I - 1)(1/R_1 - 1/R_2)$, where $R_1$ and $R_2$ are the radii of curvature of the two surfaces of the intraocular lens. Therefore, the $\lambda$ dependence of $n_I$ makes the intraocular lens optical power $P_I$ also depend on the wavelength $\lambda$: $P_I = P_I(\lambda)$. It is noted that this dependence involves the sign of the optical power of the lens. For positive optical power lenses, the typically negative $\partial n_I/\partial \lambda < 0$ translates to a negative $\partial P_I/\partial \lambda < 0$ whereas for negative optical powers, the negative $\partial n_I/\partial \lambda < 0$ translates to a positive $\partial P_I/\partial \lambda < 0$.

With these introductory remarks, an intraocular lens can compensate chromatic aberrations, if the wavelength derivative of its optical power compensates the negative wavelength derivative of the eye optical power, so that $\partial P_I/\partial \lambda + \partial P_e/\partial \lambda \approx 0$. In other words, $\partial P_I/\partial \lambda \approx -\partial P_e/\partial \lambda > 0$.

Now, since regular (non-diffractive) intraocular lenses deliver a positive optical power $P_I$ of about 20D, in the light of the introductory remarks, their $\partial P_I/\partial \lambda$ is negative, and thus they are unable to compensate the eye's own chromatic aberrations, because $\partial P_e/\partial \lambda$ is also negative.

However, embodiments of the CLA IOL 100 are made of two different lenses, the IOL 110, and the light adjustable lens 120. Such two-lens designs introduce a genuinely new possibility. One of the lenses of the CLA IOL 100 can have a negative optical power and thus a strongly positive $\partial P/\partial \lambda > 0$, so that the combined, two-lens CLA IOL 100 can compensate the chromatic aberration of the eye optical system, while the combined optical powers of the two lenses can still perform the primary function of the intraocular lens, to deliver about 20D. In formulae, the first lens optical power $P_{I,1}$ and the second lens optical power $P_{I,2}$ of a two-lens CLA IOL 100 can simultaneously satisfy the following two relations:

$$P_{I,1} + P_{I,2} = 20D, \tag{1}$$

$$\partial P_{I,1}/\partial \lambda + \partial P_{I,2}/\partial \lambda \approx -\partial P_e/\partial \lambda > 0 \tag{2}$$

In some detail, FIGS. 10A-B show embodiments of the CLA IOL 100 which deliver such reduced chromatic aberrations. Traditionally, in such composite lenses, the negative optical power lens is often referred to as a "flint", the positive optical power lens as a "crown". If the composite lens itself exhibits near zero chromatic aberration, then the CLA IOL 100 can be called an "achromat". If the composite lens makes a larger assembly, such as the CLA IOL 100 plus the eye, exhibit near zero chromatic aberration, then the CLA IOL 100 can be called an "achromator".

FIG. 10A shows an embodiment where the IOL 110, having a negative optical power $P_{IOL}<0$, is the flint, and the light adjustable lens (LAL) 120, having a positive optical power $P_{LAL}>0$, is the crown. FIG. 10B illustrates an opposite embodiment, where the IOL 110 has a positive power $P_{IOL}>0$, and the light adjustable lens 120 has a negative power $P_{LAL}<0$.

The magnitude of $\partial n/\partial \lambda$, $|\partial n/\partial \lambda|$ is relatively high for PMMA, while $|\partial n/\partial \lambda|$ is typically low for silicone. Therefore, CLA IOLs 100 embodiments with the design of FIG. 10A, where the negative power IOL 110 is made of PMMA, or other acrylates or analogs, and the positive power light adjustable lens 120 is made of silicone, can reduce the chromatic aberration efficiently. In this embodiment, the high $|\partial n/\partial \lambda|$ PMMA IOL 110 can be given a low and negative optical power, such as $P_{IOL} \approx -10D$, while the low $|\partial n/\partial \lambda|$ silicone LAL 120 can be given a high optical power, $P_{LAL} \approx +30D$, so that the combined optical power of the entire CLA IOL 100 is:

$$P_{IOL}+P_{LAL} \approx +20D, \quad (3)$$

while at the same time the CLA IOL 100 is still capable of compensating the chromatic aberration of the eye:

$$\partial P_{IOL}/\partial \lambda + \partial P_{LAL}/\partial \lambda \approx -\partial P_e/\partial \lambda \quad (4)$$

Such a CLA IOL 100 can deliver an overall optical power of about 20D, while the combined wavelength derivatives of the optical powers of the IOL 110 and the LAL 120 can largely compensate the chromatic aberrations of the eye optical system, thereby substantially reducing the overall chromatic aberration of the eye after the implantation of the CLA IOL 100. (Here, the "eye optical system" primarily refers to the cornea, as the crystalline lens has been removed by the cataract surgery.)

FIG. 11 illustrates the above concepts in the language of the chromatic shifts. The chromatic shift characterizes the distance of the image from the target/image plane (in the case of the eye, from the retina), expressed in diopters. A negative chromatic shift represents that the image was formed proximal, in front of the retina, whereas a positive chromatic shift that the image was formed distal, behind the retina. Thus, the chromatic shift increasing with the wavelength represents that the optical power decreases with the wavelength: $\partial P/\partial \lambda <0$.

FIG. 11 shows that the natural eye optical system alone has an increasing chromatic shift, consistent with $\partial P_e/\partial \lambda <0$. A one component IOL 110 alone typically also has an increasing chromatic shift, consistent with $\partial P_{IOL}/\partial \lambda <0$. The dashed "composite light adjustable IOL" line indicates that if a chromatic aberration-compensating embodiment of the CLA IOL 100 is implanted into the eye, then the combined CLA IOL 100 plus eye system can exhibit minimal chromatic shift and chromatic aberration.

Accordingly, in embodiments of the CLA IOL 100, the IOL 110 has an IOL chromatic shift variation; the light adjustable lens 120 has a light adjustable lens chromatic shift variation; an eye, with a crystalline lens removed, has an eye chromatic shift variation; and a chromatic shift variation of the eye, with the composite light adjustable intraocular lens 100 implanted, can be less than a chromatic shift variation of the eye with the crystalline lens in place, wherein the chromatic shift variation is defined from a difference of a chromatic shift at 450 nm and at 650 nm.

In embodiments of the CLA IOL 100, an optical power of the IOL 110 can be negative; an optical power of the light adjustable lens 120 can be positive; and the chromatic shift variation of the eye, with the composite light adjustable intraocular lens implanted, can be less than 0.5D. In other embodiments, this chromatic shift variation can be less than 0.2D. In eyes with such achromator CLA IOLs 100 implanted, the blurriness of the image, caused by the chromatic dispersion, can be substantially smaller than that of the natural eye, thereby sharpening the vision in an additional aspect: a clear further medical benefit.

Ideas about achromator IOLs with related aspects has been proposed by E. J. Fernandez and P. Artal in an article entitled: "Achromatic doublet intraocular lens for full aberration correction", at p. 2396, vol. 8 (2017) of the Biomedical Optics Express, the paper hereby being incorporated by reference in its entirety. While instructive in some aspects, this paper did not discuss, among others, aspects of light adjustability of the involved IOLs. Adapting the technology of this paper for light adjustable lenses involves further advanced concepts.

Figure 12A:
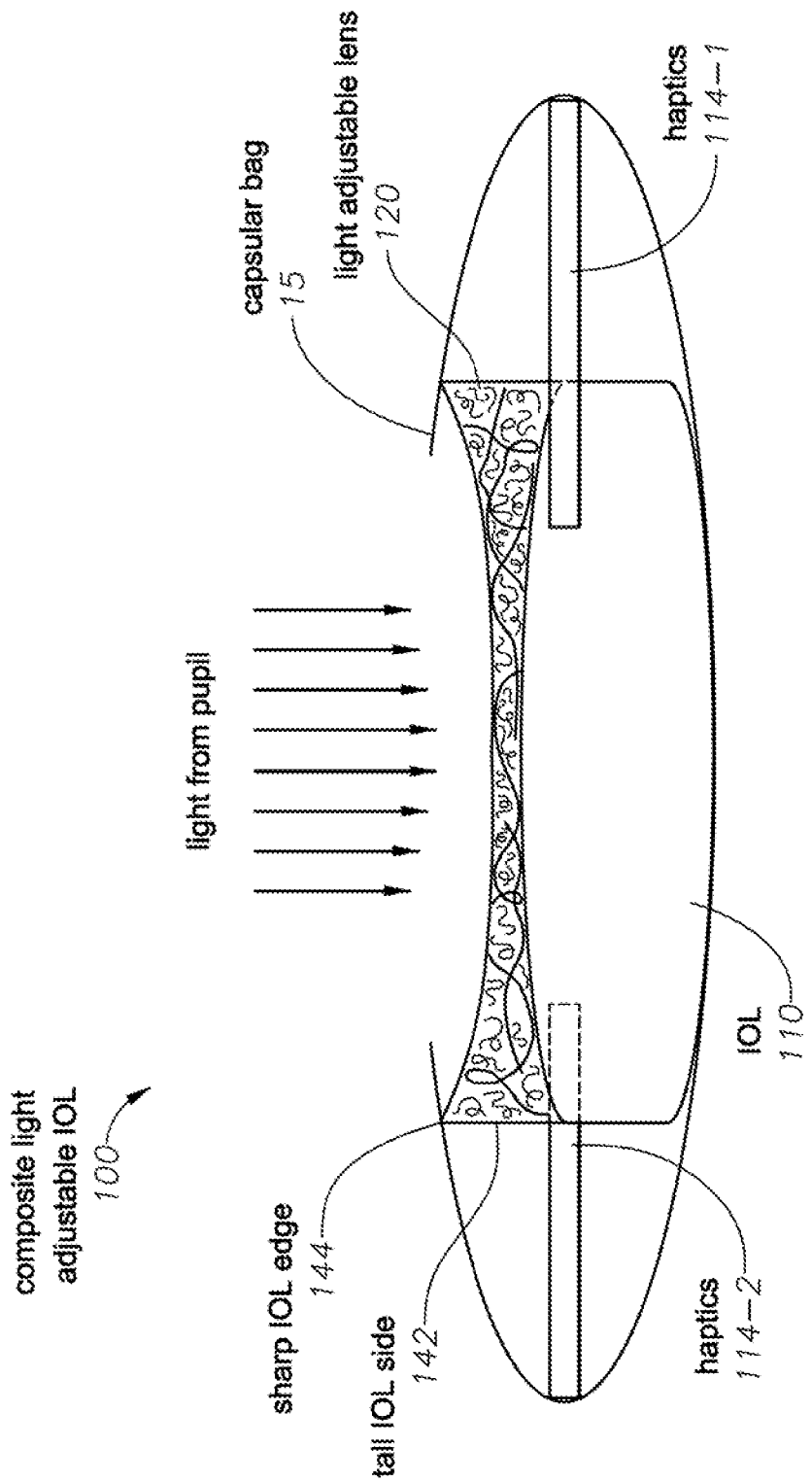
FIGS. 12A-B illustrate PCO-suppressing aspects of an achromatic embodiment of the composite light adjustable IOL.
Figure 12B:
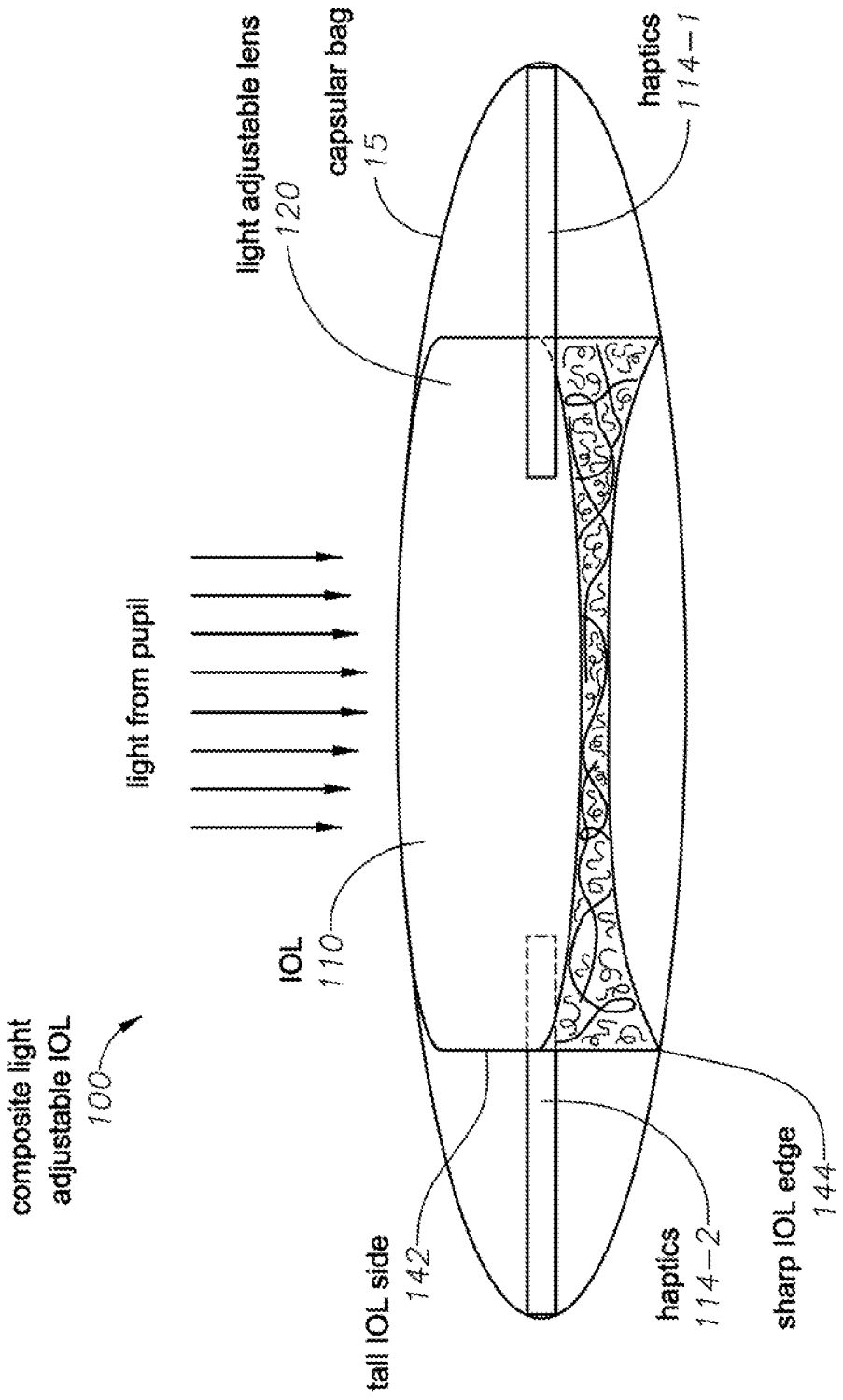

FIGS. 12A-B illustrate a further medical benefit of CLA IOLs 100, especially those where either the IOL 110, or the light adjustable lens 120 has a negative optical power, and therefore has an unusually tall side 142 and a sharp IOL edge 144. In such embodiments, the sharp IOL edge 144 may be pushed against a capsular bag 15 of the eye in which it was inserted, by a force larger than the force pushing one component intraocular lenses.

This enhanced force can have the following notable medical benefit. Posterior capsule opacification, PCO, is one of the well-known negative outcomes, or complications, of cataract surgery. PCO results from the growth and abnormal proliferation of lens epithelial cells (LECs) on the posterior capsule. Most PCOs are fibrous, or pearl-like, or a combination of both. Clinically, PCO can be detected as a wrinkling on the posterior capsule, for example. The development of PCO often involves three basic phenomena: proliferation, migration and differentiation of residual LECs.

While various pharmaceutical solutions have been developed to mitigate PCO, forming a sharp mechanical barrier in contact with the capsular bag 15 was also shown to reduce PCO. Such a barrier suppresses the fibrous growth and reduces LEC migration, thereby reducing PCO.

In embodiments of the CLA IOL 100, the sharp IOL edge 144 is pushed against the capsular bag 15 with unusually high force because the flint lens of the achromat has an unusually tall side 142 since it has negative optical power and thus its side is taller than its center. For this reason, achromat embodiments of the CLA IOL 100 exhibit the additional medical benefit of PCO reduction.

FIG. 12A and FIG. 12B illustrate that there can be several combinations and designs of the CLA IOL 100 that press the capsular bag 15 with higher than usual force. For example, the sequence of the IOL 110 and the light adjustable lens 120 can be reversed. In other embodiments, the materials of the flint and the crown can be exchanged. CLA IOLs 100 that have a distal crown lens, i.e. a crown lens that is closer to the retina can exhibit advantageously lower aberrations, as the distalmost surface of such CLA IOLs 100 is closest in shape to the shape of the retina. In contrast, if the flint is closer to the retina, then the distalmost surface is substantially different from the surface of the retina, giving rise to higher aberrations.

Yet another medical benefit of these CLA IOLs 100 with tall sides is that the higher pressing forces induce higher capsular bag tensions. This higher capsular tension tends to stabilize the location and the axis of the CLA IOL 100 better than the lower capsular tension induced by the flat regular IOLs, thereby preventing the CLA IOL 100 from tilting, or otherwise getting misaligned.

The taller IOL side 142 may necessitate the formation of a larger, or longer, surgical incision. This, in turn, may induce an unintentional astigmatism after the cataract surgery. However, since the light adjustable lens 120 can be adjusted after the surgery, in embodiments of the CLA IOL 100, this astigmatism can be compensated and eliminated efficiently by applying an astigmatism-compensating light adjustment procedure to the light adjustable lens 120.

Figure 13:
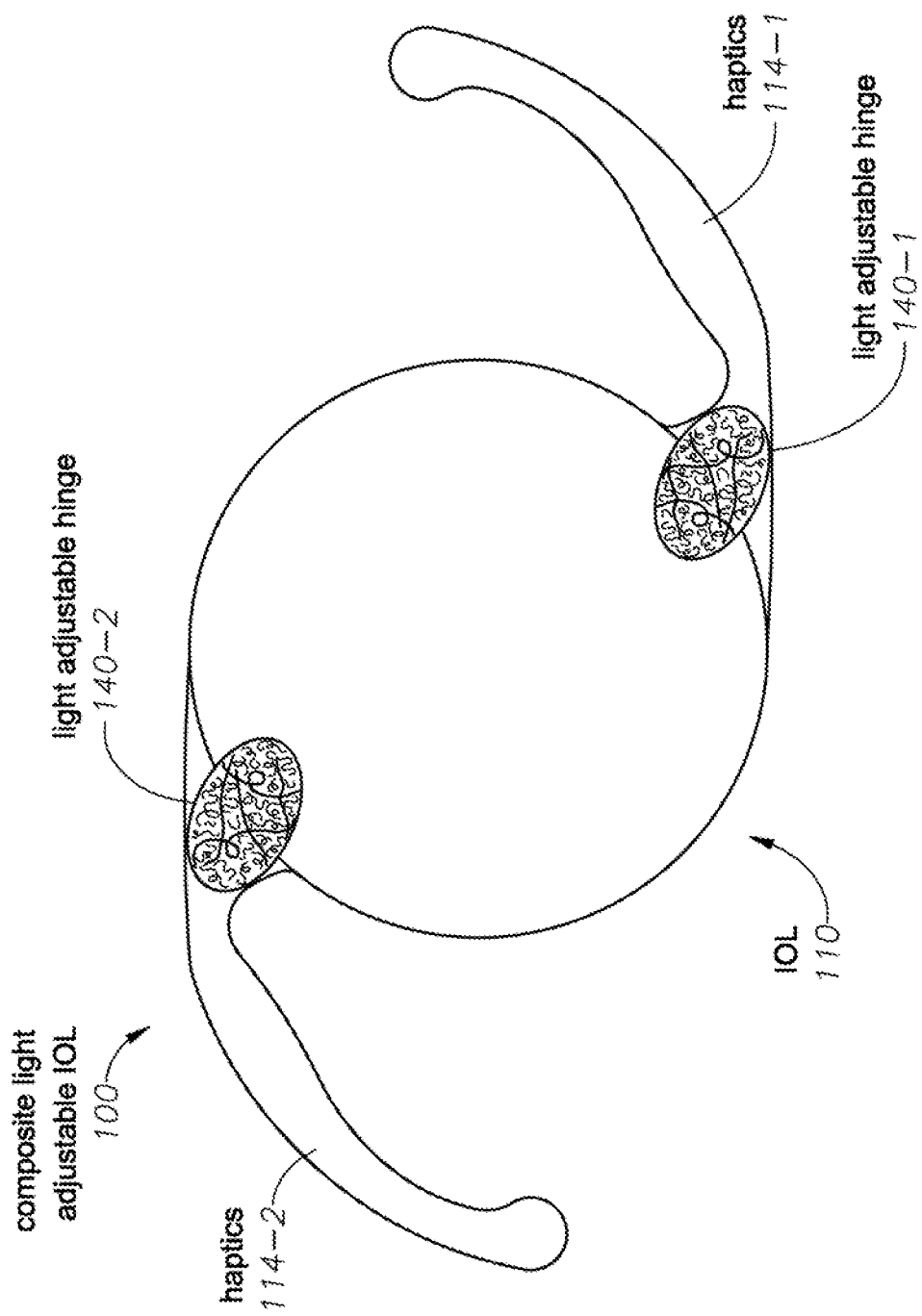
FIG. 13 illustrates an embodiment of a composite light adjustable IOL with light adjustable hinges.

FIGS. 13-14 illustrate embodiments of the composite light adjustable IOL 100 that include the IOL 110, and haptics 114 that are attached to the IOL 110 with light-adjustable hinges 140. In these embodiments, the light adjustability of the CLA IOL 100 is primarily provided not by adjusting an optical property of a light adjustable lens 120, but by changing a shape of the light adjustable hinges 140, and thereby adjusting a mechanical relation between the IOL 110 and its haptics 114. For example, when a relative angle of the haptics 114 is modified relative to the IOL 110, this shifts or rotates the IOL 110 inside the capsule of the eye, thereby adjusting the optical performance or power of the entire CLA IOL 100. For brevity and clarity, below the haptics 114-1 and 114-2 will be sometimes summarily referred to as haptics 114, and the corresponding light adjustable hinges 140-1 and 140-2 as light adjustable hinges 140. While below two-haptic-two hinge embodiments will be described expressly, CLA IOLs 100 with one, two, three or more haptics 114, and with one, two, three or more light adjustable hinge 140 can perform analogous functions.

Figure 14A:
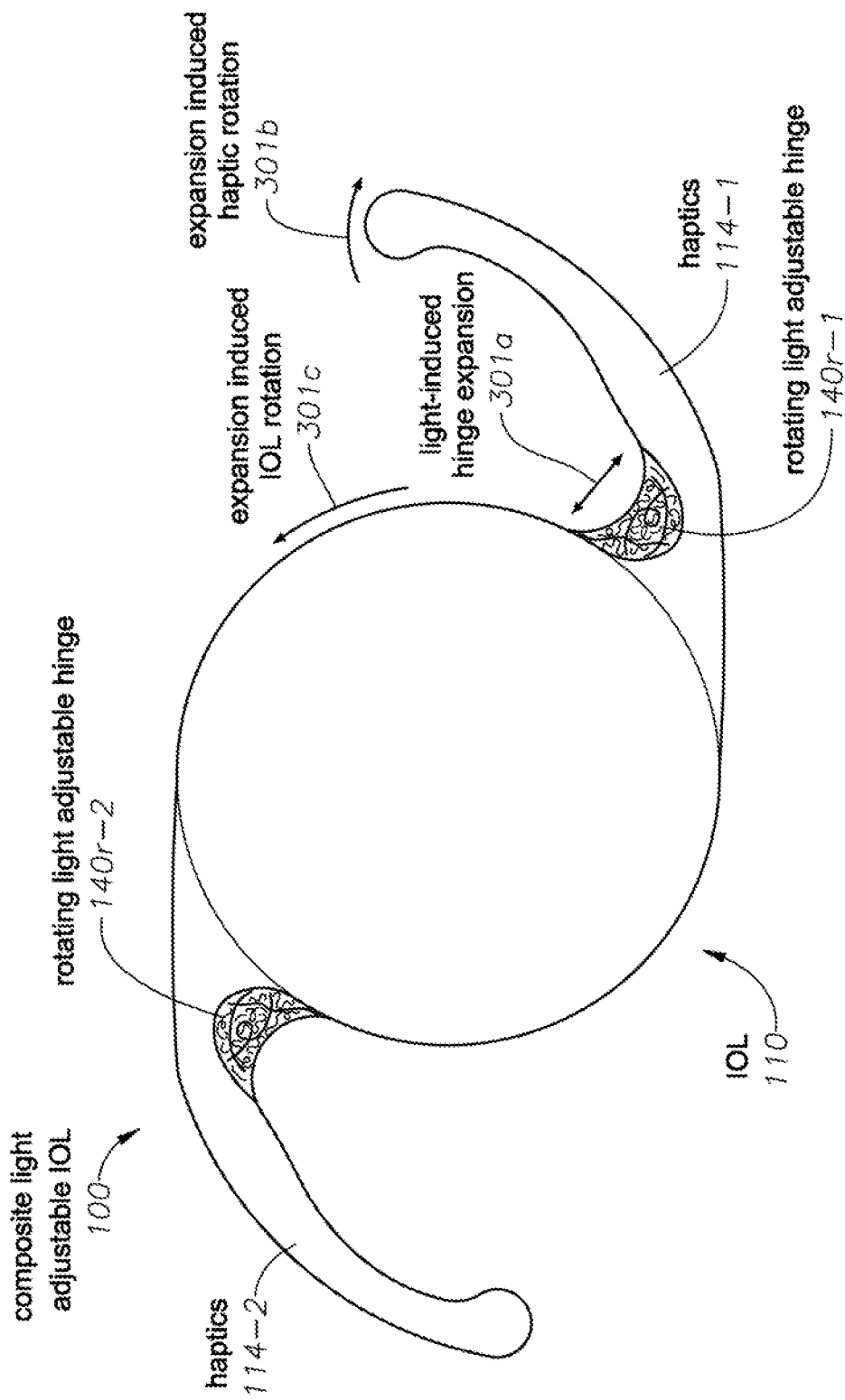
FIGS. 14A-C illustrate embodiments of composite light adjustable IOL with rotating and tilting light adjustable hinges.

FIG. 14A illustrates an embodiment where the light-adjustable hinges 140-1 and 140-2 are adapted to rotate the CLA IOL 100, and hence referred to as rotating light-adjustable hinges 140r-1 and 140r-2. These rotating light adjustable hinges, collectively 140r, are configured to change their shape upon illumination, thereby adjusting an angle between the haptics 114 and the IOL 110, inducing a haptic rotation, and thereby inducing a rotation of the IOL 110.

Detailing the steps, applying an illuminating light can generate a light-induced hinge expansion 301a. This expansion 301a can induce a haptic rotation 301b relative to the capsule 15, which can then cause an expansion induced IOL rotation 301c. Such embodiments can counter-rotate a toric CLA IOL 100 whose toric axis got unintentionally rotated after implantation, analogously to the steps and embodiments described in FIGS. 7A-C, FIGS. 8A-C and FIG. 9.

Figure 14B:
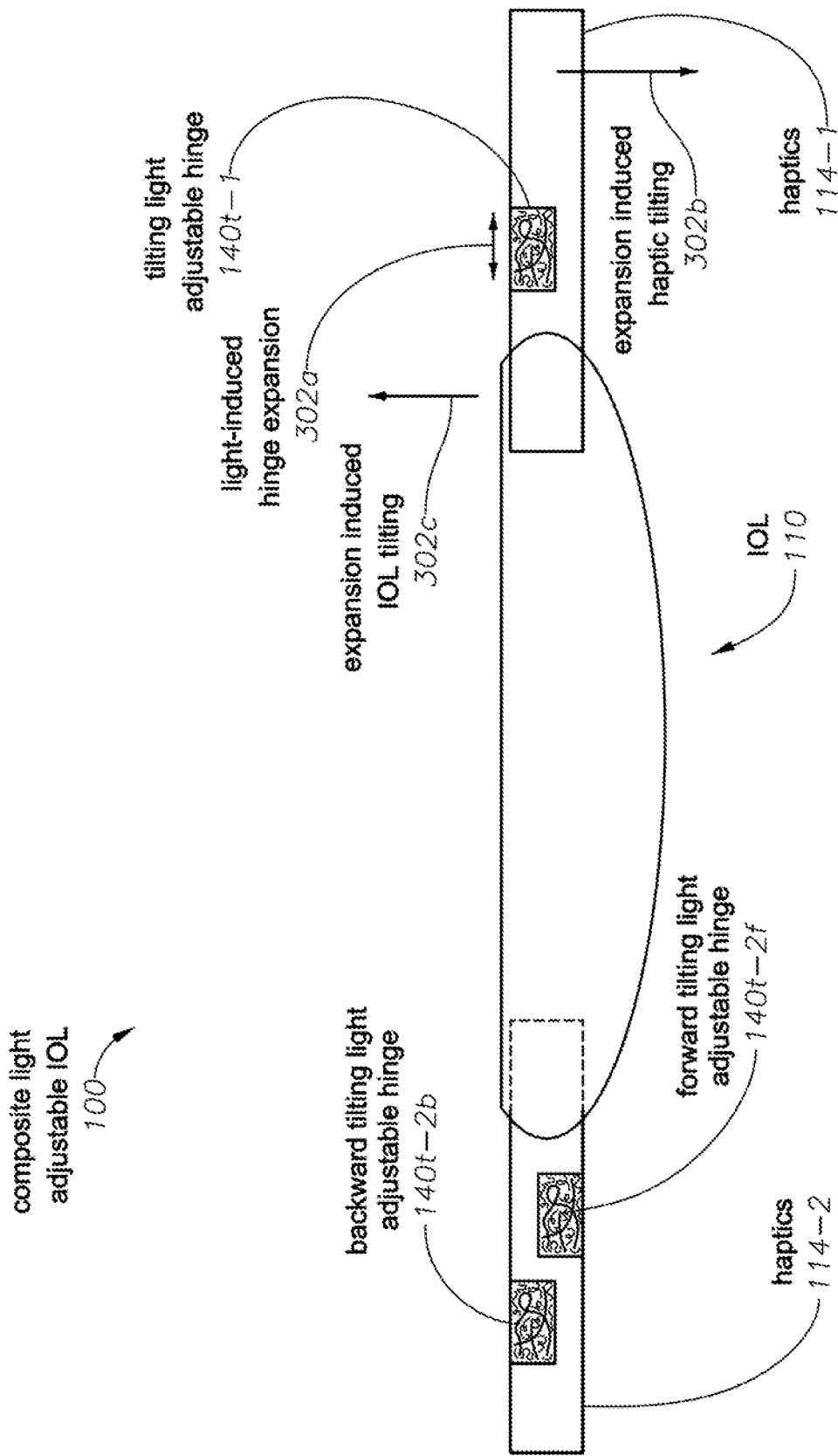

FIG. 14B illustrates a related embodiment of the CLA IOL 100, where the light-adjustable hinges 140 are tilting light-adjustable hinges 140t-1 and 140t-2 (detailed further below). These tilting light adjustable hinges 140t are configured to change a shape upon illumination, thereby tilting the haptics 114 relative to the IOL 110, and thereby inducing a tilting of the CLA IOL 100 itself.

Detailing the steps, applying an illuminating light can generate a light-induced hinge expansion 302a. This expansion 302a can induce an expansion induced haptic 302b, which can cause an expansion induced IOL tilting 302c.

In some embodiments, both forward and backward tilting adjustability can be reached by installing two tilting hinges 140 for each haptic 114: a forward tilting light adjustable hinge 140t-2f, and a backward tilting light adjustable hinge 140t-2b. Visibly, the expansion 302a of the forward tilting hinge 140t-2f can tilt the IOL 110 forward, and the expansion 302a of the backward tilting hinge 140t-2b can tilt the IOL 110 backward.

It is noted that in the above embodiments the light-induced expansion 301a or 302a of the light-adjustable hinges 140r or 140t modifies an angle of the haptics 114 relative to the IOL 110 where these two meet. Therefore, the long arms of the haptics 114 greatly amplify the expansion of the light adjustable hinges 140r or 140t in the manner of a lever arm. Therefore, relatively small expansions of the light adjustable hinges 140 can lead to an amplified, and therefore medically beneficial rotation and tilting of the IOL 110.

Figure 14C:
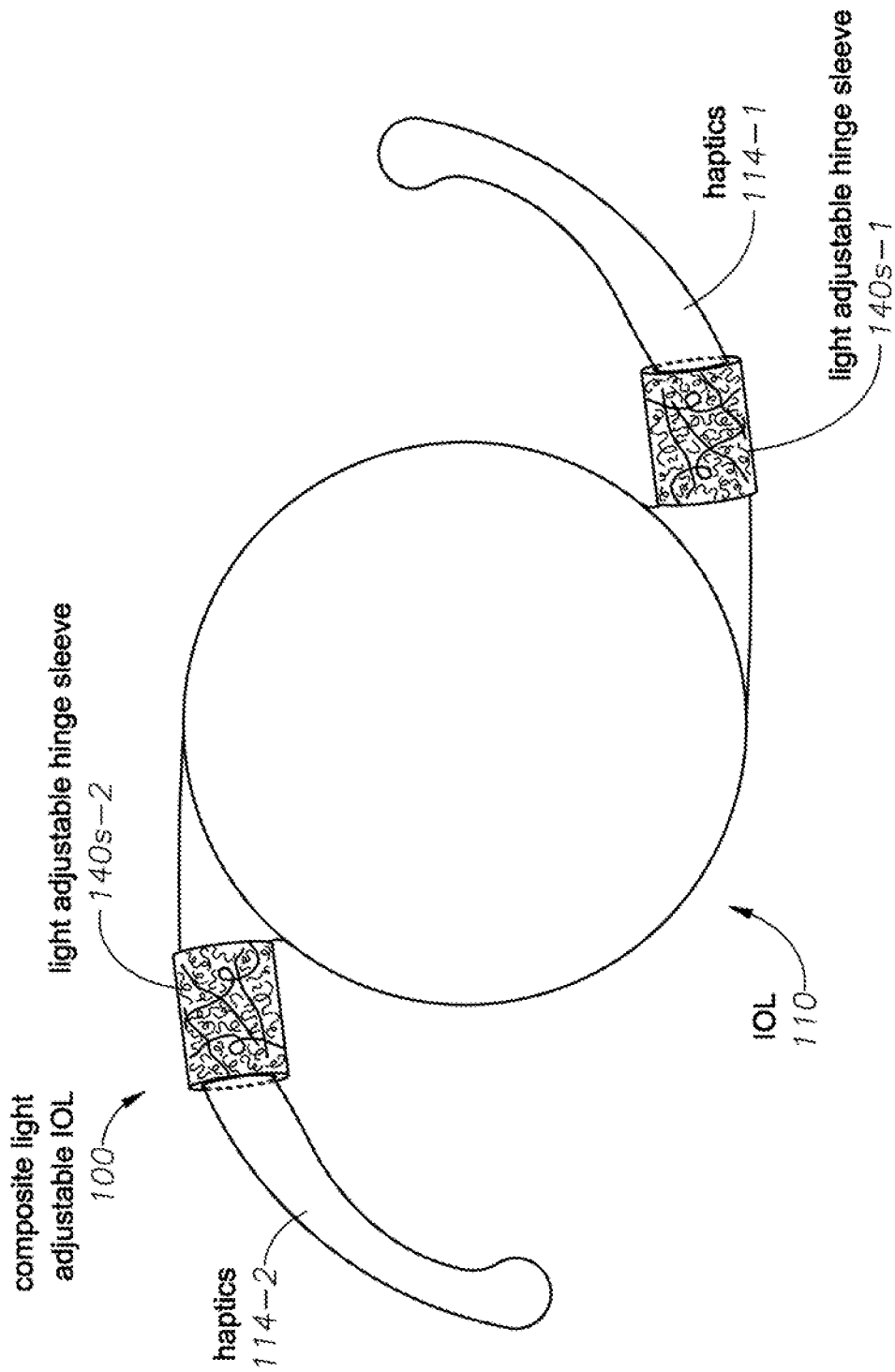

FIG. 14C illustrates that many other designs of the light adjustable hinges can deliver related functionalities. These include the combinations of rotating hinges 140r and tilting hinges 140t, as well as light adjustable rings, levers, and actuators. Notable among them are cylindrical light adjustable hinge sleeves 140s. These cylindrical light adjustable hinge sleeves 140s-1 and 140s-2 can be simply slipped onto the haptics 114 and pushed and attached to the point of juncture with the IOL 110. Applying an illumination to any part of the cylindrical sleeve 140s will push, or rotate, the IOL 110 to the opposite direction. Any of the described light adjustable hinges 140, including 140r, 140t, and 140s, can move the IOL 110 inside the eye after cataract surgery non-invasively, thus adjusting and improving its optical performance and medical benefits.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

The invention claimed is:

1. A composite light adjustable intraocular lens, comprising:
   an intraocular lens (IOL);
   a light adjustable lens, attached to the intraocular lens at one of a proximal surface and a distal surface of the IOL, the light adjustable lens including
     a first polymer matrix; and
     a refraction modulating composition, dispersed in the first polymer matrix; wherein
     the refraction modulating composition is capable of stimulus-induced polymerization that modulates a refraction of the light adjustable lens; and
   haptics.

2. The composite light adjustable intraocular lens of claim 1, characterized by at least one of:
   the haptics being attached to the IOL;
   the haptics being molded together with the IOL;
   the haptics being attached to the light adjustable lens; and
   the haptics being attached to both the IOL and the light adjustable lens.

3. The composite light adjustable intraocular lens of claim 1, the IOL comprising:
   at least one of a monomer, a macromer, and a polymer, including
     at least one of an acrylate, an alkyl acrylate, an aryl acrylate, a substituted aryl acrylate, a substituted alkyl acrylate, a vinyl, and copolymers combining alkyl acrylates and aryl acrylates.

4. The composite light adjustable intraocular lens of claim 3, the alkyl acrylate comprising:
a methyl acrylate, an ethyl acrylate, a phenyl acrylate, and polymers and co-polymers thereof.

5. The composite light adjustable intraocular lens of claim 3, the IOL further comprising:
at least one of silicone-based monomers and macromers, forming at least one of polymers and copolymers with at least one of an acrylate, an alkyl acrylate, an aryl acrylate, a substituted aryl acrylate, a substituted alkyl acrylate, a vinyl, and copolymers combining alkyl acrylates and aryl acrylates.

6. The composite light adjustable intraocular lens of claim 3, wherein:
at least one of a monomer, a macromer, and a polymer of the IOL is having at least one functional group, wherein the functional group
includes at least one of hydroxy, amino, and vinyl, mercapto, isocyanate, nitrile, carboxyl, hydride, and is one of cationic, anionic and neutral.

7. The composite light adjustable intraocular lens of claim 1, the first polymer matrix comprising:
a siloxane based polymer, formed from macromer and monomer building blocks with at least one of an alkyl group and an aryl group.

8. The composite light adjustable intraocular lens of claim 1, the first polymer matrix comprising:
at least one of an acrylate, an alkyl acrylate, an aryl acrylate, a substituted aryl acrylate, a substituted alkyl acrylate, a vinyl, and copolymers combining alkyl acrylates and aryl acrylates,
forming at least one of polymers and copolymers with compounds of the first polymer matrix.

9. The composite light adjustable intraocular lens of claim 1, the light adjustable lens comprising:
a photoinitiator,
to absorb a refraction modulating illumination;
to be activated upon the absorption of the illumination; and
to initiate the polymerization of the refraction modulating compound.

10. The composite light adjustable intraocular lens of claim 9, the photoinitiator comprising:
an ultraviolet-absorber.

11. The composite light adjustable intraocular lens of claim 1, wherein:
the refraction modulating composition is not soluble in the IOL.

12. The composite light adjustable intraocular lens of claim 1, wherein:
an elastic constant of the IOL is softer than a corresponding elastic constant of the light adjustable lens.

13. The composite light adjustable intraocular lens of claim 1, the light adjustable lens comprising at least one of:
an ultraviolet absorbing layer at a distal surface of the light adjustable lens; and
an ultraviolet absorbing material dispersed throughout the light adjustable lens.

14. The composite light adjustable intraocular lens of claim 1, wherein:
the light adjustable lens is attached to the IOL at a proximal surface of the IOL; and
the IOL includes at least one of
an ultraviolet absorbing material dispersed throughout the IOL; and
an ultraviolet absorbing layer.

15. The composite light adjustable intraocular lens of claim 1, wherein:
the light adjustable lens is attached to the IOL by at least one of a chemical reaction, a thermal treatment, an illumination treatment, a polymerization process, a molding step, a curing step, a lathing step, a cryo-lathing step, a mechanical process, an application of an adhesive, and by a combination thereof.

16. The composite light adjustable intraocular lens of claim 1, comprising:
an attachment structure, for attaching the light adjustable lens to the IOL.

17. The composite light adjustable intraocular lens of claim 16, wherein:
the attachment structure includes at least one of a cylinder, a ring, an open tub, and a clasp.

18. The composite light adjustable intraocular lens of claim 1, wherein:
the IOL is one of a multifocal IOL, an aspheric IOL, and a diffractive IOL.

19. The composite light adjustable intraocular lens of claim 1, wherein:
the IOL is a toric IOL.

20. The composite light adjustable intraocular lens of claim 19, wherein:
the IOL is the toric IOL for correcting a cylinder greater than 2D; and
the light adjustable lens is adapted to be able to correct a cylinder up to 2D.

21. The composite light adjustable intraocular lens of claim 1, wherein:
the IOL has an IOL chromatic shift variation;
the light adjustable lens has a light adjustable lens chromatic shift variation; and
a chromatic shift variation of an eye, with a crystalline lens removed and the composite light adjustable intraocular lens implanted, is less than a chromatic shift variation of the eye with the crystalline lens in place, wherein
the chromatic shift variation is defined from a difference of a chromatic shift at 450 nm and at 650 nm.

22. The composite light adjustable intraocular lens of claim 21, wherein:
an optical power of the IOL is negative;
an optical power of the light adjustable lens is positive; and
the chromatic shift variation of the eye, with the composite light adjustable intraocular lens implanted, is less than 0.5D.

23. A composite light adjustable intraocular lens, comprising:
an intraocular lens (IOL); and
haptics, attached to the IOL with light-adjustable hinges that include
a first polymer matrix; and
a refraction modulating composition, dispersed in the first polymer matrix; wherein
the refraction modulating composition is capable of stimulus-induced polymerization; and
the light-adjustable hinges are rotating light-adjustable hinges, to change shape upon illumination, thereby adjusting an angle between the haptics and the IOL, without changing the refractive power of the IOL.

* * * * *